US012220484B2

(12) United States Patent
Haas et al.

(10) Patent No.: US 12,220,484 B2
(45) Date of Patent: *Feb. 11, 2025

(54) STABLE FORMULATIONS OF LIPIDS AND LIPOSOMES

(71) Applicant: BioNTech SE, Mainz (DE)

(72) Inventors: Heinrich Haas, Mainz (DE); Isaac Hernan Esparza Borquez, Mainz (DE)

(73) Assignee: BioNTech SE, Mainz (DE)

( * ) Notice: Subject to any disclaimer, the term of this patent is extended or adjusted under 35 U.S.C. 154(b) by 683 days.

This patent is subject to a terminal disclaimer.

(21) Appl. No.: 17/495,104

(22) Filed: Oct. 6, 2021

(65) Prior Publication Data

US 2022/0023212 A1 Jan. 27, 2022

Related U.S. Application Data

(63) Continuation of application No. 15/510,973, filed as application No. PCT/EP2015/071344 on Sep. 17, 2015, now Pat. No. 11,173,120.

(51) Int. Cl.
A61K 9/127 (2006.01)
A61K 9/00 (2006.01)
A61K 31/713 (2006.01)

(52) U.S. Cl.
CPC .......... *A61K 9/1272* (2013.01); *A61K 9/0019* (2013.01); *A61K 31/713* (2013.01)

(58) Field of Classification Search
CPC .. A61K 9/1272; A61K 9/0019; A61K 31/713; A61K 47/186; A61K 47/24; A61K 47/28; A61K 9/08; A61K 9/127; A61K 31/7088; A61K 47/12; A61K 47/14; A61P 43/00
USPC ........................................................ 424/450
See application file for complete search history.

(56) References Cited

U.S. PATENT DOCUMENTS

| | | |
|---|---|---|
| 4,897,355 A | 1/1990 | Eppstein et al. |
| 5,264,618 A | 11/1993 | Felgner et al. |
| 5,703,055 A | 12/1997 | Felgner et al. |
| 5,965,542 A | 10/1999 | Wasan et al. |
| 6,034,137 A | 3/2000 | Belloni et al. |
| 6,251,399 B1 | 6/2001 | Diamond et al. |
| 6,372,498 B2 | 4/2002 | Newman et al. |
| 6,413,544 B1 | 7/2002 | Smyth-Templeton et al. |
| 6,472,176 B2 | 10/2002 | Kovesdi et al. |
| 6,500,641 B1 | 12/2002 | Chen et al. |
| 6,586,410 B1 | 7/2003 | Wheeler et al. |
| 7,303,881 B2 | 12/2007 | Huang et al. |
| 7,462,354 B2 | 12/2008 | Sette et al. |
| 7,790,696 B2 | 9/2010 | Gregoriadis |
| 8,140,270 B2 | 3/2012 | Kingsmore et al. |
| 8,217,016 B2 | 7/2012 | Hoerr et al. |
| 8,349,558 B2 | 1/2013 | Fatho et al. |
| 8,703,142 B2 | 4/2014 | Diamond et al. |
| 8,853,283 B2 | 10/2014 | Platscher et al. |
| 8,877,206 B2 | 11/2014 | Chen et al. |
| 9,115,402 B2 | 8/2015 | Hacohen et al. |
| 9,707,299 B2 | 7/2017 | Muro-Galindo et al. |
| 11,173,120 B2 | 11/2021 | Haas et al. |
| 2004/0071768 A1 | 4/2004 | Sarris et al. |
| 2006/0147513 A1 | 7/2006 | Papahadjopoulos et al. |
| 2006/0159737 A1 | 7/2006 | Panzner et al. |
| 2006/0257465 A1 | 11/2006 | Maurer et al. |
| 2007/0025968 A1 | 2/2007 | Van Der Burg et al. |
| 2007/0134154 A1 | 6/2007 | Chang et al. |
| 2007/0207194 A1 | 9/2007 | Grayburn et al. |
| 2008/0193511 A1 | 8/2008 | Massing |
| 2009/0055944 A1 | 2/2009 | Korman et al. |
| 2009/0217401 A1 | 8/2009 | Korman et al. |
| 2012/0021042 A1 | 1/2012 | Panzner et al. |
| 2012/0087975 A1 | 4/2012 | Mundus et al. |
| 2012/0237975 A1 | 9/2012 | Schrum et al. |
| 2013/0028962 A1 | 1/2013 | Zhang et al. |
| 2013/0115272 A1 | 5/2013 | de Fougerolles et al. |
| 2013/0115274 A1 | 5/2013 | Knopov et al. |
| 2013/0123481 A1 | 5/2013 | de Fougerolles et al. |
| 2013/0156849 A1 | 6/2013 | de Fougerolles et al. |
| 2013/0203115 A1 | 8/2013 | Schrum et al. |
| 2013/0237593 A1 | 9/2013 | de Fougerolles et al. |

(Continued)

FOREIGN PATENT DOCUMENTS

| | | |
|---|---|---|
| CA | 2271325 A1 | 5/1998 |
| CA | 2816925 | * 11/2011 |

(Continued)

OTHER PUBLICATIONS

Hui, S. et al., The Role of Helper Lipids in Cationic Liposome-Mediated Gene Transfer, Biophysical Journal, 71:590-599 (1996).
Ozpolat, B. et al., Liposomal siRNA nanocarriers for cancer therapy, Advanced Drug Delivery Reviews, 66:110-116 (2014).
Nov. 30, 2018—(EP) Office Action—App. 15763367.8.
Apr. 2, 2019—(JP) Office Action—App. 2017-516418.
Jan. 21, 2019—(SG) Written Opinion—Application No. 11201702182Y.
Agrawal et al., Trend in Biotechnology, 14(10): 376-387, 1996.
Bei et al., J Immunother., 21(3):159-69 (1998).
Boczkowski et al., Dendritic cells pulsed with RNA are potent antigen-presenting cells in vitro and in vivo, J Exp. Med., 184:465-472 (1996).

(Continued)

*Primary Examiner* — Frederick F Krass
*Assistant Examiner* — Lucy M Tien
(74) *Attorney, Agent, or Firm* — Choate, Hall & Stewart LLP; Brenda Herschbach Jarrell; Michael A. Shinall

(57) ABSTRACT

The present invention relates to aqueous lipid and/or liposome formulations with an increased chemical stability, to methods of preparing such aqueous formulations as well as to kits comprising them. The present invention further relates to methods of preparing lipid-based pharmaceutical compositions, to pharmaceutical compositions prepared by such methods and to methods of chemically stabilizing aqueous lipid and/or liposome formulations.

20 Claims, 9 Drawing Sheets

(56) References Cited

U.S. PATENT DOCUMENTS

| | | | |
|---|---|---|---|
| 2013/0237594 A1 | 9/2013 | de Fougerolles et al. |
| 2013/0244278 A1 | 9/2013 | de Fougerolles et al. |
| 2013/0244279 A1 | 9/2013 | de Fougerolles et al. |
| 2013/0245106 A1 | 9/2013 | de Fougerolles et al. |
| 2013/0245107 A1 | 9/2013 | de Fougerolles et al. |
| 2013/0255281 A1 | 10/2013 | Bray |
| 2013/0266640 A1 | 10/2013 | de Fougerolles et al. |
| 2014/0010861 A1 | 1/2014 | Bancel et al. |
| 2014/0147454 A1 | 5/2014 | Chakraborty et al. |
| 2015/0017211 A1 | 1/2015 | de Fougerolles et al. |
| 2015/0030576 A1 | 1/2015 | Bancel |
| 2015/0167017 A1 | 6/2015 | Roy et al. |
| 2015/0252372 A1 | 9/2015 | Chang et al. |
| 2016/0002667 A1 | 1/2016 | Kaufman et al. |
| 2017/0273907 A1 | 9/2017 | Haas et al. |

FOREIGN PATENT DOCUMENTS

| | | |
|---|---|---|
| CN | 102858153 A | 1/2013 |
| CN | 103906503 A | 7/2014 |
| EP | 0839912 A1 | 5/1998 |
| EP | 1242108 A1 | 9/2002 |
| EP | 2569633 A2 | 3/2013 |
| JP | 2005-535730 A | 11/2005 |
| JP | 4975964 * | 7/2012 |
| WO | WO-1994/023031 A1 | 10/1994 |
| WO | WO-95/35094 A1 | 12/1995 |
| WO | WO-1998/014464 A1 | 4/1998 |
| WO | WO-1999/024566 A1 | 5/1999 |
| WO | WO-1999/052503 A2 | 10/1999 |
| WO | WO-2000/20029 A1 | 4/2000 |
| WO | WO-2000/067761 A1 | 11/2000 |
| WO | WO-2001/047959 A2 | 7/2001 |
| WO | WO-2001/093902 A2 | 12/2001 |
| WO | WO-2002/048377 A2 | 6/2002 |
| WO | WO-2002/083714 A2 | 10/2002 |
| WO | WO-02/098443 A2 | 12/2002 |
| WO | WO-2003/051401 A2 | 6/2003 |
| WO | WO-2003/068257 A1 | 8/2003 |
| WO | WO-2003/106692 A2 | 12/2003 |
| WO | WO-2004/002453 A1 | 1/2004 |
| WO | WO-2004/002468 A1 | 1/2004 |
| WO | WO-2004/004743 A1 | 1/2004 |
| WO | WO-2005/030250 A2 | 4/2005 |
| WO | WO-2005/039533 A1 | 5/2005 |
| WO | WO-2005/040816 A1 | 5/2005 |
| WO | WO-2005/110338 A2 | 11/2005 |
| WO | WO-2006/121168 A1 | 11/2006 |
| WO | WO-2007/024708 A2 | 3/2007 |
| WO | WO-2007/025760 A2 | 3/2007 |
| WO | WO-2007/031222 A2 | 3/2007 |
| WO | WO-2007/101227 A2 | 9/2007 |
| WO | WO-2008/080468 A1 | 7/2008 |
| WO | WO-2008/083174 A2 | 7/2008 |
| WO | WO-2008/085562 A2 | 7/2008 |
| WO | WO-2008/116078 A2 | 9/2008 |
| WO | WO-2008/147526 A1 | 12/2008 |
| WO | WO-2008/156712 A1 | 12/2008 |
| WO | WO-2009/053041 A2 | 4/2009 |
| WO | WO-2009/118296 A2 | 10/2009 |
| WO | WO-2009/129227 A1 | 10/2009 |
| WO | WO-2010/066418 A1 | 6/2010 |
| WO | WO-2010/105209 A1 | 9/2010 |
| WO | WO-2011/012316 A2 | 2/2011 |
| WO | WO-2011/143656 A2 | 11/2011 |
| WO | WO-2012/045075 A1 | 4/2012 |
| WO | WO-2012/045082 A2 | 4/2012 |
| WO | WO-2012/135805 A2 | 10/2012 |
| WO | WO-2012/159729 A1 | 11/2012 |
| WO | WO-2013/040142 A2 | 3/2013 |
| WO | WO-2013/052523 A1 | 4/2013 |
| WO | WO-2013/064911 A2 | 5/2013 |
| WO | WO-2013/090648 A1 | 6/2013 |
| WO | WO-2013/124701 A2 | 8/2013 |
| WO | WO-2013/151663 A1 | 10/2013 |
| WO | WO-2013/151664 A1 | 10/2013 |
| WO | WO-2013/151665 A2 | 10/2013 |
| WO | WO-2013/151672 A2 | 10/2013 |
| WO | WO-2014/012051 A1 | 1/2014 |
| WO | WO-2014/071219 A1 | 5/2014 |
| WO | WO-2014/093924 A1 | 6/2014 |
| WO | WO-2014/144039 A1 | 9/2014 |
| WO | WO-2014/144711 A1 | 9/2014 |
| WO | WO-2014/144767 A1 | 9/2014 |
| WO | WO-2014/152027 A1 | 9/2014 |
| WO | WO-2014/152030 A1 | 9/2014 |
| WO | WO-2014/152031 A1 | 9/2014 |
| WO | WO-2014/152211 A1 | 9/2014 |
| WO | WO-2014/159813 A1 | 10/2014 |
| WO | WO-2014/160243 A1 | 10/2014 |
| WO | WO-2014/164253 A1 | 10/2014 |
| WO | WO-2014/168874 A2 | 10/2014 |
| WO | WO-2015/014375 A1 | 2/2015 |
| WO | WO-2015/034925 A1 | 3/2015 |
| WO | WO-2015/034928 A1 | 3/2015 |
| WO | WO-2015/038892 A1 | 3/2015 |
| WO | WO-2015/043613 A1 | 4/2015 |
| WO | WO-2015/051169 A2 | 4/2015 |
| WO | WO-2015/051173 A2 | 4/2015 |
| WO | WO-2015/058780 A1 | 4/2015 |
| WO | WO-2015/085318 A2 | 6/2015 |
| WO | WO-2015/089511 A2 | 6/2015 |
| WO | WO-2015/117620 A1 | 8/2015 |
| WO | WO-2015/164674 A1 | 10/2015 |
| WO | WO-2015/172843 A1 | 11/2015 |
| WO | WO-2016/045732 A1 | 3/2016 |
| WO | WO-2016/062323 A1 | 4/2016 |
| WO | WO-2016/091391 A1 | 6/2016 |
| WO | WO-2016/107877 A1 | 7/2016 |
| WO | WO-2016/155809 A1 | 10/2016 |

OTHER PUBLICATIONS

Bowerman, NA., Engineering the binding properties of the T cell receptor: peptide: MHC ternary complex that governs T cell activity, Mol. Immun., 46:3000-3008 (2009).
Brickner et al. J Exp. Med 193(2) 195-205 (2001).
Chen et al., An overview of liposome lyophilization and its future potential, J Controlled Release, 142(3):299-311 (2010).
Conry et al., Characterization of a messenger RNA polynucleotide vaccine vector, Cancer Res,. 55:1397-1400 (1995).
Conry et al., Immune response to a carcinoembryonic antigen polynucleotide vaccine, Cancer Res., 54:1164-1168 (1994).
Coulie et al., A mutated intron sequence codes for an antigenic peptide recognized by cytolytic T lymphocytes on a human melanoma, Proc. Natl. Acad. Sci. USA, 92:7976-7980 (1995).
De La Torre, L. G et al., The synergy between structural stability and DNA-binding controls the antibody production in EPC/DOTAP/DOPE liposomes and DOTAP/DOPE lipoplexes, Colloids and Surfaces B: Biointerfaces, 73:175-184 (2009).
Del Val et al., Cell, 66(6):1145-1153 (1991).
Dengjel, J et al. Glycan side chains on naturally presented MHC class II ligands J Mass Spectrom, 2005.
Ding et al. Genome remodeling in a basal-like breast cancer metastasis and xenograft Nature, 464: 999-1005, 2010.
Dolgin, Nature 522:26.
Dolgin, The Billion-Dollar Biotech, Nature, 522:26-28, Jun. 4, 2015.
Fenske et al., Entrapment of small molecules and nucleic acid-based drugs in liposomes, Methods Enzymol, 391:7-40 (2005).
Fritsch, E. F. et al. HLA-Binding Properties of Tumor Neoepitopes in Humans Cancer Immunology Research, 2: 522-529, 2014.
Gnirke, A. Solution hybrid selection with ultra-long oligonucleotides for massively parallel targeted sequencing Nat. Biotechnol, 2009.
Goya, R. et al. SNVMix: predicting single nucleotide variants from next-generation sequencing of tumors, Bioinformatics Bioinformatics, 26: 730-736, 2010.
Grit et al., Chemical stability of liposomes: implications for their physical stability, Chemistry and Physics of Lipids, 64:3-18 (1993).

(56) References Cited

OTHER PUBLICATIONS

Grit et al., Hydrolysis of phosphatidylcholine in aqueous liposome dispersions, International Journal of Pharmaceutics, 50:1-6 (1989).
Grit, M et al., Hydrolysis of Saturated Soybean Phosphatidylcholine in Aqueous Liposome Dispersions, Journal of Pharmaceutical Sciences, 82(4): 362-366 (1993).
Gryaznov et al., Biochim. Biophys. Acta, 1489: 131-140, 1999.
Guyre et al., Cancer Immunother, 45:146-148 (1997).
Hacohen Decl. dated Feb. 16, 2014 filed in U.S. Appl. No. 13/108,610, 10 pages.
Hoerr et al., In vivo application of RNA leads to induction of specific cytotoxic T lymphocytes and antibodies, Eur. J. Immunol., 30:1-7 (2000).
How Long Can I Store Liposomes?, Avanti Polar Lipids, retreived on Jul. 19, 2020 from https://avantilipids.com/tech-support/faqs/liposomes-shelf-life, 2 pages.
How Should I Store My Liposomes?, Avanti Polar Lipids, retreived on Jul. 19, 2020 from http://avantilipids.com/tech-support/faqs/liposome-storage, 2 pages.
Hydrolysis and Oxidation of Liposomes, Encapsula NanoSciences, retreived on Aug. 21, 2020 from https://encapsula.com/hydrolysis-and-oxidation-of-liposomes/, 5 pages.
International Preliminary Report on Patentability Chapter I, Dated Mar. 28, 2017, Filed in relation to PCT Application No. PCT/EP2014/070503, Filed Sep. 25, 2014, Entitled Stable Formulations of Lipids and Liposomes, By Applicant "BioNTech RNA Pharmaceuticals GmbH," 7 pages.
International Preliminary Report on Patentability Chapter I, Dated Mar. 28, 2017, Filed in relation to PCT Application No. PCT/EP2015/071344, Filed Sep. 17, 2015, Entitled Stable Formulations of Lipids and Liposomes, By Applicant "BioNTech RNA Pharmaceuticals GmbH," 7 pages.
International Search Report (ISR), Dated Dec. 14, 2015, Filed in relation to PCT Application No. PCT/EP2015/071344, Filed Sep. 17, 2015, Entitled "Stable Formulations of Lipids and Liposomes," By Applicant "BioNTech RNA Pharmaceuticals GmbH," 4 pages.
International Search Report (ISR), Dated Jul. 8, 2015, Filed in relation to PCT Application No. PCT/EP2014/070503, Filed Sep. 25, 2014, Entitled "Stable Formulations of Lipids and Liposomes," Bv Aoolicant "BioNTech RNA Pharmaceuticals GmbH," 4 pages.
Johanning et al., Nucleic Acids Res., 23(9):1495-1501 (1995).
Kenter, G. G. et al. Phase I Immunotherapeutic Trial with Long Peptides Spanning the E6 and E7 sequences of High-risk human papillomavirus 16 in End-stage cervical cancer patients shows low toxicity and robust immunogenicity. Clinical Cancer Research, 14: 169-177, 2008.
Keogh, E. et al. Identification of New Epitopes from Four Different Tumor-Associated Antigens: Recognition of Naturally Processed Epitopes Correlates with HLA-A*0201-Binding Affinity, J. Immunol. 167: 787-796, 2001.
Lemmel, Claudia et al., Differential quantitative analysis of MHC ligands by mass spectrometry using stable isotope labeling Nat Biotechnol, 2004.
Lennerz et al., The response of autologous T cells to a human melanoma is dominated by mutated heoantigens, Proc. Natl. Acad. Sci. USA, 102:16013-16018 (2005).
Ley et al., DNA sequencing of a cytogenetically normal acute myeloid leukaemia genome, Nature, 456:66-72 (2008).
Li et al., Cancer Genome Sequencing and Its Implications for Personalized Cancer Vaccine, Cancer, 3:1191-4211 (2011).
Maksyutov and Zagrebelnaya, ADEPT: a computer program for prediction of protein antigenic determinants, Comput. Appl. Biosci., 9:291-297 (1993).
Mandelboim et al., Regression of established murine carcinoma metastases following vaccination with tumour-associated antigen peptides, Nature Medicine, 1:1179-1183 (1995).
Mardis, ER., Recurring Mutations Found by Sequencing an Acute Myeloid Leukemia Genome, New England J. Med., 361:1058-1066 (2009).
Margulies, Marcel et al., Genome Sequencing in Open Microfabricated High Density Picoliter Reactors Nature, 2005.
Martinon et al., Induction of virus-specific cytotoxic T lymphocytes in vivo by liposome- entrapped mRNA, Eur. J. Immunol, 23:1719-1722 (1993).
Mayer et al., Anticancer Research 25:3917-3924 (2005).
Mayer et al., Characterization of liposomal systems containing doxorubicin entrapped in response to pH gradients, Biochim Biophys Acta, 1025(2):143-51 (1990).
Meyerson, M. et al. Advances in understanding cancer genomes through second-generation sequencing Nature Rev. Genetics. 11:685-695, 2010.
Monach et al., A unique tumor antigen produced by a single amino acid substitution, Immunity, 2:45-59 (1995).
Mortazavi, Mapping and quantifying mammalian transcriptomes by RNA-Seq, Nature Methods, 5:621-628 (2008).
Parker et al., J. Immunol., 152:163-175 (1994).
Parkhurst, MR. et al. Improved Induction of Melanoma-reactive CTL with peptides from the melanoma antigen gp100 modified at HLA-A*0201-binding residues. J Immunol. 157: 2549-2548, 1996.
Parmiani, G et al., Unique Human Tumor Antigens: Immunobiology and Use in Clinical Trials, The Journal of mmunology, 178:1975-1979 (2007).
Perissi et al., Electron Spin Resonance and Differential Scanning Calorimetry as Combined Tools for the Study of iposomes in the Presence of Long Chain Nitroxides, 106 J. of Phys. Chem. B 10468 (2002).
Pfohl et al., Biological Polyelectrolyte Complexes in Solution and Confined on Patterned Surfaces, 198-200 Colloids & Surfaces A: Physicochemical and Eng. Aspects 613 (2002).
Pilla, L. et al. Multipeptide vaccination in cancer patients Expert Opinion on Biological Therapy, 9: 1043-1055, 2009.
Pleasance, E. et al. A small-cell lung cancer genome with complex signatures of tobacco exposure. Nature, 463: 184-190, 2010.
Pleasance, E. et al., A comprehensive catalogue of somatic mutations from a human cancer genome, Nature, 463:191-196 (2010).
U.S. Appl. No. 61/334,866, filed May 14, 2010.
Rammansee, Chapter 50: Cancer Vaccines: Some Basic Considerations, Genomic and Personalized Medicine, Hungtington and Ginsburg. E-published on Nov. 11, 2008.
Rammensee et al., Immunogenentics, 50:213-219 (1999).
Rammensee et al., Toward patient-specific tumor antigen selection for vaccination, Immunol. Rev, 188:164-176 (2002).
Rammensee, Some considerations on the use of peptides and mRNA for therapeutic vaccination against cancer, Immunol Cell Biol., 84(3):290-4 (2006).
Rao, Epitope-based vaccines: One step at a time, Proc. Indian natn. Sci. Acad., B60:419-424 (1994).
Remaut, K et al., Influence of plasmid DNA topology on the transfection properties of DOTAP/DOPE lipoplexes, Journal of Controlled Release, 115:335-343 (2006).
Ressing, M et al. Human CTL epitopes encoded by human papillomavirus types 16E6. J Immunol. 154:5934-5943, 1995.
Saenz-Badillos et al., RNA as a tumor vaccine: a review of the literature, Exp Dermatol., 10(3):143-54 (2001).
Segal et al., Epitope landscape in breast and colorectal cancer, Cancer Res. 68: 889-892 (2008).
Sensi and Aanichini, Unique Tumor Antigens: Evidence for Immune Control of Genome Integrity and Immunogenic Targets forT cell-mediated Patient-Specific Immunotherapy, Clin. Cancer Res., 12(17), 5023 (2006).
Sette, A. et al. Peptide Binding to the Most Frequent HLA-A Class I Alleles Measured by Quantitative Molecular Binding Assays Mol. Immunol. 31: 813-822, 1994.
Sette, A. et al. The Relationship Between Class I Binding Affinity and Immunogenicity of Potential Cytotoxic T cell Epitopes. J Immunol. 153: 5586-5592, 1994.
Shah et al., Mutation of FOXL2 in granulosa-cell tumors of the ovary, N. Eng. J. Med., 360:2719-2729 (2009).
Sjoblom et al., The consensus coding sequences of human breast and colorectal cancers, Science 314:268-274 (2006).

(56) References Cited

OTHER PUBLICATIONS

Stark et al., Long-term stability of sterically stabilized liposomes by freezing and freeze-drying: Effects of cryoprotectants on structure, European J Pharm. Sci, 41(3-4):546-555 (2010).
Stephens et al., A screen of the complete protein kinase gene family identifies diverse patterns of somatic mutations in human breast cancer, Nature Genetics, 37:590-592 (2005).
Thomson et al., J. Virology, 72(3):2246-2252 (1998).
Toes et al., Protective anti-tumor immunity induced by vaccination with recombinant adenoviruses encoding 9 multiple tumor-associated cytotoxic T lymphocyte epitopes in a string-of-beads fashion, Proc. Natl. Acad. Sci. USA, 94:14660-14665 (1997).
UniProtKB—P36888 (FLT3_HUMAN), last sequence update: Aug. 21, 2007.
UniProtKB—Q5SW79 (CE170_HUMAN), last sequence update: Dec. 21, 2004.
UniProtKB—Q9NVD7 (Parva_Human), last sequence update: Oct. 1, 2000.
UniProtKB, "Print-outs from the UniProtKB database concerning the CEP170, Parva and FLT3 genes."
Van der Bruggen et al., A gene encoding an antigen recognized by cytolytic T lymphocytes on a human melanoma, Science, 254:1643-1647 (1991).
Van Laere, AS, et al. A regulatory mutation in IGF2 causes a major QTL effect on muscle growth in the pig, Nature, 425(6960):832-836 (2003).
Van Winden, E. et al., Strategies for large scale production and optimized stability of pharmaceutical liposomes developed for parenteral use, Lasic and Papahadjopoulous (eds,.), Medical Applications of Liposomes, 567-604 (1998).
Van Winden, et al., Short term stability of freeze-dried, lyoprotected liposomes, J Controlled Release, 58(1):69-86 (1999).
Vernooij et al., Chemical hydrolysis of DOT AP and DOPE in a liposomal environment, Journal of Controlled Release, 79:299-303 (2002).
Weinschenk et al., Integrated functional genomics approach for the design of patient-individual antitumor vaccines, Cancer Res, 62:5818-5827 (2002).
Wolff, et al., Direct gene transfer into mouse muscle in vivo, Science 247:1465-1468 (1990).
Wood et al., The genomic landscapes of human breast and colorectal cancers, Science, 318:1108-1113 (2007).
Wortzel et al., Multiple tumour-specific antigens expressed on a single tumour cell, Nature, 304:165-167 (1983).
Written Opinion issued in related Singapore Application No. 11201702182Y, dated Feb. 12, 2018.
Written Opinion of the International Search Authority, Dated Dec. 14, 2015, Filed in relation to PCT Application No. PCT/EP2015/071344, Filed Sep. 17, 2015, Entitled Stable Formulations of Lipids and Liposomes, By Applicant "BioNTech RNA Pharmaceuticals GmbH," 6 pages.
Written Opinion of the International Search Authority, Dated Jul. 8, 2015, Filed in relation to PCT Application No. PCT/EP2014/070503, Filed Sep. 25, 2014, Entitled "Stable Formulations of Lipids and Liposomes," By Applicant "BioNTech RNA Pharmaceuticals GmbH," 6 pages.
Zhou et al., Hum. Gene Ther., 10(16):2719-24, 1999.
Zuidam et al., Chemical Hydrolysis of Phospholipids, Journal of Pharmaceutical Sciences, 84(9) Sep. 1995.

* cited by examiner

STABLE FORMULATIONS OF LIPIDS AND LIPOSOMES

TECHNICAL FIELD OF THE INVENTION

The present invention relates to aqueous lipid and/or liposome formulations with an increased chemical stability, to methods of preparing such aqueous formulations as well as to kits comprising them. The present invention further relates to methods of preparing lipid-based pharmaceutical compositions, to pharmaceutical compositions prepared by such methods and to methods of chemically stabilizing aqueous lipid and/or liposome formulations.

BACKGROUND OF THE INVENTION

Lipids in water may exist in different forms of lamellar or non-lamellar (e.g., cubic or hexagonal) phases, which are often denominated as lyotropic lipid phases. For example, liposomes consist of uni- or multilamellar self-closed lipid bilayers dispersed in water. In more general terms, they may be considered as colloidal systems where the lipids are organized in a lamellar form. Many of these systems comprising lyotropic lipid phases are of interest as pharmaceutical formulations for drug delivery or other applications. One requirement for bringing such lipid-based pharmaceutical products into clinical practice is that a sufficient shelf-life after manufacturing can be provided. Here, besides other criteria, chemical stability of the liposome forming lipids may be a limiting factor. Liposomes are typically assembled from phospholipids or related compounds. Phospholipids consist of fatty acids, linked to a triglyceride backbone via ester bonds. These ester bonds are prone to chemical hydrolysis, which is accelerated under acidic or basic conditions (acidic or basic ester hydrolysis). If the liposomes or other systems that are present as lyotropic lipid phases are to be stored several months or years in the aqueous phase, ester hydrolysis may become a limiting factor for shelf-life stability.

In view of the acceleration of ester hydrolysis under acidic or basic conditions, the best stability or lowest hydrolysis rate for lipids is normally expected to be in a pH range of between 6 and 7. Other options to prevent hydrolysis are freezing and/or lyophilization of the liposomes (Chen et al., 2010; van Winden and Crommelin, 1999; Stark et al., 2010). Protocols for freezing and lyophilization of liposomes are reported in the literature. However, these additional technical steps make manufacturing also more complicated and more expensive. In many cases, it is required that cryoprotectants are added, which may not be possible or desirable for certain products. For example, the presence of cryoprotectants and/or freezing/lyophilization itself may affect the product properties in an undesired way. Therefore, the long-term stabilization of liquid liposome preparations is still an unmet need. In this context, there is a considerable interest in techniquesto minimi 7P hydrolysis of liposomes or, more generally speaking, colloidally dispersed lipids in the liquid (aqueous) phase. This is particularly the case if the liposomes are intended for use as pharmaceutical products because in that case the stabilization method must fulfill the regulatory and technological requirements for such products. Most challenging in this context are products for parenteral (e.g. intravenous) administration, where, inter alia, certain criteria relating to sterility, selection of excipients, ion and pH conditions or particulate composition must be fulfilled.

The present invention aims at providing methods and means to increase the stability, particularly the chemical stability of lipids and/or liposomes formulated in aqueous formulations, thereby increasing the shelf-life stability of these formulations.

SUMMARY OF THE INVENTION

In a first aspect, the present invention relates to an aqueous formulation comprising
   at least one lipid having one or more bonds selected from the group consisting of ester bonds, thioester bonds and amide bonds, and
   at least one pH adjusting agent,
wherein the aqueous formulation has a pH of between 2 and 5.5.

In one embodiment, at least one of the lipids present in the aqueous formulation is a cationic lipid. In one embodiment, the cationic lipid is a cationic lipid as defined herein.

In one embodiment, the overall net charge of the lipids present in the aqueous formulation is positive.

In one embodiment, the aqueous formulation has a pH of between 2 and 5, preferably of between 2.5 and 5 more preferably of between 3 and 4.5, more preferably of between 3 and 4, and even more preferably of between 3.5 and 4.

In one embodiment, the at least one lipid having one or more bonds selected from the group consisting of ester bonds, thioester bonds and amide bonds comprises a glycerolipid and/or a glycerophospholipid.

In one embodiment, the at least one lipid having one or more bonds selected from the group consisting of ester bonds, thioester bonds and amide bonds comprises a cationic lipid and/or a non-cationic lipid.

In one embodiment, the cationic lipid is selected from the group consisting of 1,2-dioleoyl-3-trimethylammoniumpropane (DOTAP), 1,2-dioleoyloxy-3-dimethylammoniumpropane (DODAP) and analogues of these molecules having a different composition of the acyl chain moiety.

In one embodiment, the non-cationic lipid is a neutral lipid, wherein, preferably, the neutral lipid is selected from the group consisting of 1,2-di-(9Z-octadecenoyl)-sn-glycero-3-phosphoethanolamine (DOPE), 1,2-dioleoyl-sn-glycero-3-phosphocholine (DOPC), phosphatidylcholine (PC) and dimyristoyl phosphatidylcholine (DMPC).

In one embodiment, the non-cationic lipid is an anionic lipid, wherein, preferably, the anionic lipid is selected from the group consisting of phosphatidylserine (PS), phosphatidylinositol (PI), phosphatidic acid (PA), phosphatidylglycerol (PG) and dimyristoyl phosphatidylglyerol (DMPG).

In one embodiment, the aqueous formulation further comprises at least one lipid not having any ester bonds, thioester bonds or amide bonds.

In one embodiment, the at least one lipid not having any ester bonds, thioester bonds or amide bonds comprises a cationic lipid and/or a non-cationic lipid.

In one embodiment, the cationic lipid is selected from the group consisting of 1,2-di-O-octadecenyl-3-trimethylammoniumpropane (DOTMA), 1,2-dioleyloxy-N,N-dimethylaminopropane (DODMA), dioctadecyldi-methylammonium (DODA(Br)/DDAB), dioctadecyldimethylammoniumchloride (DODAC), 1,2-dimyristoyloxypropyl-1,3-dimethylhydroxyethylammonium (DMRIE), 2,3-dioleoyloxy-N-[2 (spermine carboxamide)ethyl]-N,N-dimethyl-1-propanamium trifluoroacetate (DOSPA) analogues of these molecules having a different composition of the acyl chain moiety.

In one embodiment, the non-cationic lipid is a neutral lipid, wherein, preferably, the neutral lipid is selected from the group consisting of cholesterol (Chol) and sphingomyelin (SM).

In one embodiment, the non-cationic lipid is an anionic lipid.

In one embodiment, the aqueous formulation comprises at least one cationic lipid and at least one non-cationic lipid.

In one embodiment, the molar ratio of the at least one cationic lipid to the at least one non-cationic lipid is from 1:4 to 4:1, preferably from 1:2 to 4:1.

In one embodiment, the molar fraction of the at least one cationic lipid with respect to total lipid is at least 5%, preferably at least 10%, more preferably at least 20%.

In one embodiment, the at least one pH adjusting agent comprises an acid and/or an acidic buffer.

In one embodiment, the acid is a linear, branched or cyclic $C_1$-$C_{28}$, preferably $C_1$-$C_{22}$, carboxylic acid.

In one embodiment, the acid is selected from the group consisting of acetic acid, ascorbic acid, citric acid, hydrochloric acid, phosphoric acid, branched or unbranched, saturated, monounsaturated or polyunsaturated $C_{12}$-$C_{28}$ fatty acids, preferably $C_{12}$-$C_{22}$ fatty acids (e.g. oleic acid).

In one embodiment, the acidic buffer is based on an acid as defined above.

In one embodiment, the acidic buffer is selected from the group consisting of acetate buffer, citrate buffer, phosphate buffer and carbonate buffer.

In one embodiment, the at least one pH adjusting agent comprises acetic acid and/or acetate buffer.

In one embodiment, the at least one pH adjusting agent is present in an amount such that the molar ratio of total lipid to the at least one pH adjusting agent does not exceed 100:1.

In one embodiment, the at least one pH adjusting agent is present in an amount such that the molar ratio of total lipid to the at least one pH adjusting agent is from 10:1 to 1:10, preferably from 5:1 to 1:5, more preferably from 2:1 to 1:2, more preferably from 1.5:1 to 1:1.5, even more preferably about 1:1.

In one embodiment, the hydrolysis rate of the at least one lipid having one or more bonds selected from the group consisting of ester bonds, thioester bonds and amide bonds is reduced as compared to its hydrolysis rate at a pH of between 6 and 7.

In one embodiment, the lipids present in the aqueous formulation form liposomes.

In one embodiment, the at least one pH adjusting agent is associated with the liposomes.

In a further aspect, the present invention relates to a method of preparing an aqueous formulation as defined above, the method comprising forming the liposomes in an aqueous solution comprising the at least one pH adjusting agent and having a pH of between 2 and 5.5 or adding the at least one pH adjusting agent to an aqueous solution comprising liposomes in order to adjust the pH of the aqueous solution to a pH of between 2 and 5.5.

In another aspect, the present invention relates to a kit comprising an aqueous formulation as defined above.

In one embodiment, the kit further comprises, in a separate container, a pharmaceutically active compound, wherein, preferably, the pharmaceutically active compound comprises a nucleic acid, preferably DNA or RNA.

In one embodiment, the nucleic acid is provided in a buffered solution having a pH of between 6 and 8.

In yet another aspect, the present invention relates to a method of preparing a pharmaceutical composition, the method comprising providing an aqueous formulation as defined above; and
mixing the aqueous formulation with a pharmaceutically active compound.

In one embodiment, the pharmaceutically active compound comprises a nucleic acid, preferably DNA or RNA, wherein, preferably, the nucleic acid is provided in a buffered solution having a pH of between 6 and 8.

In a further aspect, the present invention relates to a pharmaceutical composition prepared by the method as defined above.

In another aspect, the present invention relates to a method of chemically stabilizing an aqueous formulation comprising at least one lipid having one or more bonds selected from the group consisting of ester bonds, thioester bonds and amide bonds, the method comprising adjusting the pH of the aqueous formulation to a pH of between 2 and 5.5.

In one embodiment, the chemical stabilization occurs by inhibition of ester bond, thioester bond and/or amid bond hydrolysis.

In one embodiment, at least one of the lipids present in the aqueous formulation is a cationic lipid. In one embodiment, the cationic lipid is as defined above.

In one embodiment, the overall net charge of the lipids present in the aqueous formulation is positive.

In one embodiment, the pH is adjusted to a pH of between 2 and 5, preferably of between 2.5 and 5, more preferably of between 3 and 4.5, more preferably of between 3 and 4, and even more preferably of between 3.5 and 4.

In one embodiment, the pH of the aqueous lipid formulation is adjusted by adding at least one pH adjusting agent, preferably at least one pH adjusting agent as defined above.

In one embodiment, the at least one lipid having one or more bonds selected from the group consisting of ester bonds, thioester bonds and amide bonds is as defined above.

In one embodiment, the lipids present in the aqueous formulation form liposomes.

DETAILED DESCRIPTION OF THE INVENTION

Figure 1:
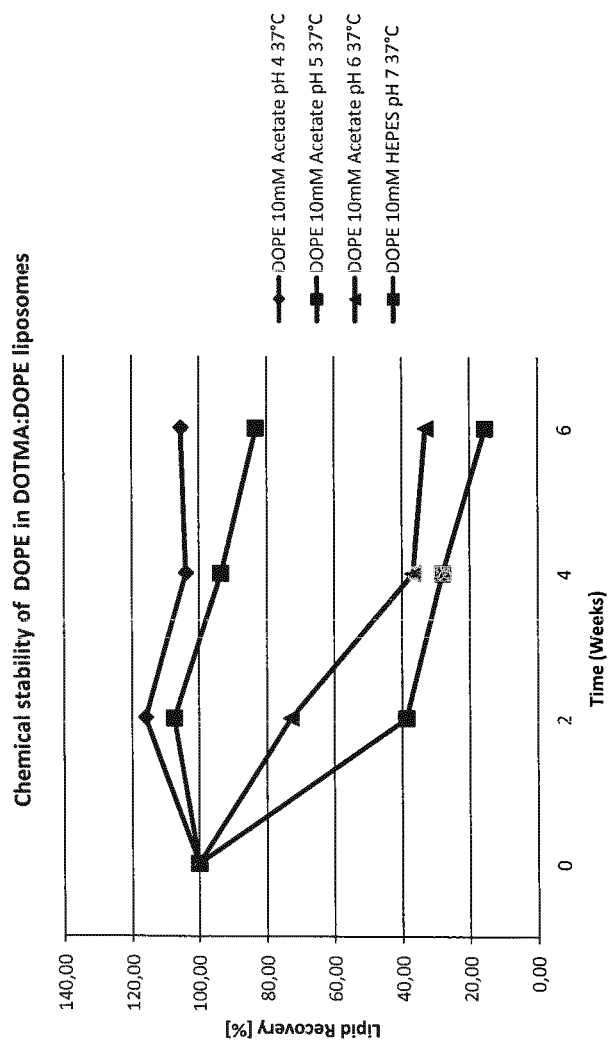
FIG. 1 shows the percentage of DOPE recovered from DOTMA/DOPE liposome dispersions prepared in dispersion solutions having different pH values. The liposome dispersion was stored at 37° C., and samples were taken at various time points.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kolbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, 2n$^d$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present invention provides an aqueous formulation comprising
  at least one lipid having one or more bonds selected from the group consisting of ester bonds, thioester bonds and amide bonds, preferably ester bonds, and
  at least one pH adjusting agent,
wherein the aqueous formulation has a pH of between 2 and 5.5.

The aqueous formulation in accordance with the present invention (which may also be referred to as aqueous lipid dispersion) is characterized by an increased chemical stability, more particularly by an increased chemical stability of the at least one lipid having one or more bonds selected from the group consisting of ester bonds, thioester bonds and amide bonds, preferably ester bonds. In one embodiment, the hydrolysis rate of the at least one lipid having one or more bonds selected from the group consisting of ester bonds, thioester bonds and amide bonds, preferably ester bonds, is reduced as compared to its hydrolysis rate at a pH of between 6 and 7. In one embodiment, the hydrolysis rate is reduced by at least factor 1.5, preferably by at least factor 2, more preferably by at least factor 3, even more preferably by at least factor 4.

In one embodiment, the aqueous formulation has a pH of between 2 and 5, preferably of between 2.5 and 5, more preferably of between 3 and 4.5, more preferably of between 3 and 4, and even more preferably of between 3.5 and 4. In a thither preferred embodiment, the aqueous formulation has a pH of between 3.1 and 3.9.

The term "lipid", as used herein, is meant to refer to an amphiphilic molecule comprising a hydrophilic moiety (e.g., a polar headgroup) and a lipophilic or hydrophobic moiety. The lipophilic or hydrophobic moiety may comprise at least one branched or linear, saturated or unsaturated fatty acid moiety or a derivative or analogue thereof (e.g., a fluorocarbon). A fatty acid moiety essentially consists of a hydrocarbon moiety/chain, particularly an acyl chain. Preferably, the fatty acid moiety or derivative or analogue thereof has a length of 10 to 30, more preferably 12 to 25, even more preferably 14 to 22 carbon atoms. In case the lipid comprises more than one, e.g. two or three, fatty acid moieties or derivatives or analogues thereof, these fatty acid moieties or derivatives or analogues thereof may be the same or different. The term "lipid" comprises cationic lipids and non-cationic lipids, i.e. neutral or anionic lipids. Lipids may include phospholipids or derivatives thereof, glycerolipids or derivatives thereof, sphingolipids (e.g., sphingomyelin) or derivatives thereof, or sterol lipids (e.g., cholesterol) or derivatives thereof. Glycerolipids are composed of glycerols that are mono-, di- or tri-substituted with fatty acid moieties. The phospholipids, whose hydrophilic moiety comprises a phosphate group, may be glycerophospholipids. Preferably, the lipids used in accordance with the present invention are bilayer-forming lipids. Lipids may also be functionalized/modified, e.g., with (oligo)peptides, polymers (e.g., PEG) or other functional groups. In an aqueous medium, lipids may further be supramolecularly organized, e.g., in the form of lipid-based particles or lyotropic phases, such as liposomes, lamellar phases, hexagonal and inverse hexagonal phases, cubic phases, micelles and reverse micelles composed of monolayers. The stabilization effect according to the present invention applies to all types of supramolecular lipid organization. Preferably, the lipids used in accordance with the present invention are pharmaceutically acceptable, e.g., suitable as excipients, as components for drug delivery formulations and/or for use in the transfection of nucleic acids into cells.

If the present disclosure refers to a charge such as a positive charge, negative charge or neutral charge or to a cationic compound, negative compound or neutral compound this generally means that the charge mentioned is present at a selected pH, such as a physiological pH. For example, the term "cationic lipid" refers to a lipid having a positive net charge at a selected pH, such as a physiological pH. The term "neutral lipid" refers to a lipid having no positive or negative net charge, which can be present in the form of a non-charge molecule or a neutral amphoteric (or zwitterionic) molecule at a selected pH, such as a physiological pH. By "physiological pH" herein is meant a pH of between 6 and 8, preferably of between 6.5 and 8, more preferably of about 7.5.

A cationic lipid preferably comprises a cationic headgroup. The polar headgroup of the cationic lipids preferably comprises amine derivatives such as primary, secondary, and/or tertiary amines, quaternary ammonium, various combinations of amines, amidinium salts, or guanidine and/or imidazole groups as well as pyridinium, piperizine and amino acid headgroups such as lysine, arginine, ornithine and/or tryptophan. More preferably, the polar headgroup of the cationic lipid comprises amine derivatives. Most preferably, the polar headgroup of the cationic lipid comprises a quaternary ammonium. The headgroup of the cationic lipid may comprise a single cationic charge or multiple cationic charges.

An anionic lipid preferably comprises an anionic headgroup, such as a phosphate group. The headgroup of the anionic lipid may comprise a single anionic charge or multiple anionic charges.

In one embodiment, at least one of the lipids present in the aqueous formulation is a cationic lipid, preferably a cationic lipid as defined herein.

In one embodiment, the overall net charge of the lipids present in the aqueous formulation is positive.

The term "overall net charge", as used herein, is meant to refer to the sum of the net charges of all lipids present in the aqueous formulation.

In one embodiment, the at least one lipid having one or more bonds selected from the group consisting of ester bonds, thioester bonds and amide bonds comprises a glycerolipid and/or a glycerophospholipid.

In one embodiment, the at least one lipid having one or more bonds selected from the group consisting of ester bonds, thioester bonds and amide bonds is a glycerolipid. In another embodiment, the at least one lipid having one or more bonds selected from the group consisting of ester bonds, thioester bonds and amide bonds is a glycerophospholipid. In yet another embodiment, the aqueous formulation comprises at least two lipids having one or more bonds selected from the group consisting of ester bonds, thioester bonds and amide bonds, wherein the at least two lipids comprise a glycerolipid and a glycerophospholipid.

In one embodiment, the at least one lipid having one or more bonds selected from the group consisting of ester bonds, thioester bonds and amide bonds comprises a cationic lipid and/or a non-cationic lipid.

In one embodiment, the at least one lipid having one or more bonds selected from the group consisting of ester bonds, thioester bonds and amide bonds is a cationic lipid. In another embodiment, the at least one lipid having one or more bonds selected from the group consisting of ester bonds, thioester bonds and amide bonds is a non-cationic lipid. In yet another embodiment, the aqueous formulation comprises at least two lipids having one or more bonds selected from the group consisting of ester bonds, thioester bonds and amide bonds, wherein the at least two lipids comprise a cationic lipid and a non-cationic lipid.

In one embodiment, the cationic lipid is selected from the group consisting of 1,2-dioleoyl-3-trimethylammoniumpropane (DOTAP), 1,2-dioleoyloxy-3-dimethylammoniumpropane (DODAP) and analogues of these molecules having a different composition of the acyl chain moiety.

In one embodiment, the non-cationic lipid is a neutral lipid, wherein, preferably, the neutral lipid is selected from the group consisting of 1,2-di-(9Z-octadecenoyl)-sn-glycero-3-phosphoethanolamine (DOPE), 1,2-dioleoyl-sn-glycero-3-phosphocholine (DOPC), phosphatidylcholine (PC) and dimyristoyl phosphatidylcholine (DMPC).

In one embodiment, the non-cationic lipid is an anionic lipid, wherein, preferably, the anionic lipid is selected from the group consisting of phosphatidylserine (PS), phosphatidylinositol (PI), phosphatidic acid (PA), phosphatidylglyerol (PG) and dimyristoyl phosphatidylglyerol (DMPG).

In one embodiment, the aqueous formulation further comprises at least one lipid not having any ester bonds, thioester bonds or amide bonds. In one embodiment, the aqueous formulation further comprises at least one lipid not having any ester bonds.

In one embodiment, the at least one lipid not having any ester bonds, thioester bonds or amide bonds comprises a glycerolipid and/or a glycerophospholipid.

In one embodiment, the at least one lipid not having any ester bonds, thioester bonds or amide bonds is a glycerolipid. In another embodiment, the at least one lipid not having any ester bonds, thioester bonds or amide bonds is a glycerophospholipid. In yet another embodiment, the aqueous formulation comprises at least two lipids not having any ester bonds, thioester bonds or amide bonds, wherein the at least two lipids comprise a glycerolipid and a glycerophospholipid.

In one embodiment, the at least one lipid not having any ester bonds, thioester bonds or amide bonds comprises a cationic lipid and/or a non-cationic lipid.

In one embodiment, the at least one lipid not having any ester bonds, thioester bonds or amide bonds is a cationic lipid. In another embodiment, the at least one lipid not having any ester bonds, thioester bonds or amide bonds is a non-cationic lipid. In yet another embodiment, the aqueous formulation comprises at least two lipids not having any ester bonds, thioester bonds or amide bonds, wherein the at least two lipids comprise a cationic lipid and a non-cationic lipid.

In one embodiment, the cationic lipid is selected from the group consisting of 1,2-di-O-octadecenyl-3-trimethylammoniumpropane (DOTMA), 1,2-dioleyloxy-N,N-dimethylaminopropane (DODMA), dioctadecyldi-methylammonium (DODA(Br)/DDAB), dioctadecyldimethylammoniumchloride (DODAC), 1,2-dimyristoyloxypropyl-1,3-dimethylhydroxyethyl ammonium (DMRIE), 2,3-dioleoyloxy-N-[2 (spermine carboxamide)ethyl]-N,N-dimethyl-1-propanamium trifluoroacetate (DOSPA) analogues of these molecules having a different composition of the acyl chain moiety.

In one embodiment, the non-cationic lipid is a neutral lipid, wherein, preferably, the neutral lipid is selected from the group consisting of cholesterol (Chol) and sphingomyelin (SM).

In one embodiment, the non-cationic lipid is an anionic lipid.

In one embodiment, the aqueous formulation comprises at least one cationic lipid and at least one non-cationic lipid, preferably at least one cationic lipid and at least one neutral lipid.

In one embodiment, the aqueous formulation comprises DOTMA and DOPE. In another embodiment, the aqueous formulation comprises DOTAP and DOPE.

In one embodiment, the non-cationic, i.e. neutral or anionic, preferably neutral, lipid functions as a "helper lipid". The term "helper lipid" refers to a lipid capable of increasing the effectiveness of delivery of lipid-based particles (e.g., liposomes) to a target, preferably into a cell.

In one embodiment, the molar ratio of the at least one cationic lipid to the at least one non-cationic lipid is from 4:1 to 1:4, preferably from 1:2 to 4:1.

In one embodiment, the molar fraction of the at least one cationic lipid with respect to total lipid is at least 5%, preferably at least 10%, more preferably at least 20%.

The term "pH adjusting agent", as used herein, is meant to refer to any pH-active agent that can be used to modify the pH value of an (aqueous) solution and includes acidifying and alkalizing agents. Acidifying agents are used to lower the pH, whereas alkalizing agents are used to increase the pH. Preferably, the pH adjusting agent in accordance with the present invention is an acidifying agent.

In one embodiment, the at least one pH adjusting agent comprises an acid and/or an acidic buffer.

In one embodiment, the acid is a linear, branched or cyclic $C_1$-$C_{28}$, preferably $C_1$-$C_{22}$, carboxylic acid.

In one embodiment, the acid is selected from the group consisting of acetic acid, ascorbic acid, citric acid, hydrochloric acid, phosphoric acid, branched or unbranched, saturated, monounsaturated or polyunsaturated $C_{12}$-$C_{28}$ fatty acids, preferably $C_{12}$-$C_{22}$ fatty acids (e.g. oleic acid).

In one embodiment, the acidic buffer is based on an acid as defined above.

In one embodiment, the acidic buffer is selected from the group consisting of acetate buffer, citrate buffer, phosphate buffer and carbonate buffer.

In one embodiment, the at least one pH adjusting agent comprises acetic acid and/or acetate buffer.

In one embodiment, the at least one pH adjusting agent is present in an amount such that the molar ratio of total lipid to the at least one pH adjusting agent does not exceed 100:1.

In one embodiment, the at least one pH adjusting agent is present in an amount such that the molar ratio of total lipid to the at least one pH adjusting agent is from 10:1 to 1:10, preferably from 5:1 to 1:5, more preferably from 2:1 to 1:2, more preferably from 1.5:1 to 1:1.5, even more preferably about 1:1.

In one embodiment, the at least one pH adjusting agent is present at a concentration of 1 mM to 10 mM.

In one embodiment, the lipids present in the aqueous formulation form lipid-based particles, such as liposomes. Accordingly, in one embodiment, the aqueous formulation is an aqueous liposome dispersion. In one embodiment, the overall net charge of the lipids forming the liposomes is positive. In one embodiment, the liposomes are cationic liposomes.

The term "liposome", as used herein, is meant to refer to a microscopic lipidic vesicle often having one or more bilayers of a vesicle-forming lipid, such as a phospholipid, and being capable of encapsulating a drug. Different types of liposomes may be employed in the context of the present invention, including, without being limited thereto, multilamellar vesicles (MLV), small unilamellar vesicles (SUV), large unilamellar vesicles (LUV), sterically stabilized liposomes (SSL), multivesicular vesicles (MV), and large multivesicular vesicles (LMV) as well as other bilayered forms known in the art. The size and lamellarity of the liposome will depend on the manner of preparation. In one embodiment, the liposomes have an average diameter in the range of from about 50 nm to about 1000 nm, preferably from about 100 nm to about 800 nm, preferably about 200 nm to about 600 nm, such as about 300 nm to about 500 nm.

Liposomes may be formed using standard methods, such as the reverse evaporation method (REV), the ethanol injection method, the dehydration-rehydration method (DRV), sonication or other suitable methods. Preferably, liposomes are formed using the ethanol injection method.

The term "ethanol injection method" refers to a process, in which an ethanol solution comprising lipids is rapidly dropped into an aqueous solution through a needle. This action disperses the lipids throughout the solution and promotes lipid-particle formation, such as liposome formation.

In one embodiment, the at least one pH adjusting agent is associated with the lipid-based particles, preferably liposomes. According to the present invention, the term "associated with" means that the pH adjusting agent is bound to or forms part of the lipid-based particles, preferably liposomes, e.g., by being incorporated/inserted into the lipid bilayer membrane. In one embodiment, the pH adjusting agent being associated with the liposomes is a carboxylic acid, preferably a carboxylic acid as defined above. In one embodiment, the carboxylic acid is a branched or unbranched $C_{12}$-$C_{28}$, preferably $C_{12}$-$C_{22}$, carboxylic acid. In one embodiment, the carboxylic acid is a branched or unbranched, saturated, monounsaturated or polyunsaturated $C_{12}$-$C_{28}$ fatty acid, preferably $C_{12}$-$C_{22}$ fatty acid (e.g., oleic acid). In one embodiment, the lipid-based particles, preferably liposomes comprise 1 to 10% of the pH adjusting agent.

In one embodiment, the lipid-based particles, preferably liposomes comprise (e.g., encapsulate) a pharmaceutically active compound, wherein, preferably, the pharmaceutically active compound comprises a nucleic acid, preferably DNA or RNA.

The present invention also provides a method of preparing an aqueous formulation as defined above, the method comprising
    forming the liposomes in an aqueous solution comprising the at least one pH adjusting agent and having a pH of between 2 and 5.5 or adding the at least one pH adjusting agent to an aqueous solution comprising liposomes in order to adjust the pH of the aqueous solution to a pH of between 2 and 5.5.

The present invention also provides a kit comprising an aqueous formulation as defined above.

In one embodiment, the kit further comprises, in a separate container, a pharmaceutically active compound, wherein, preferably, the pharmaceutically active compound comprises a nucleic acid, preferably DNA or RNA.

In one embodiment, the nucleic acid is provided in a buffered solution having a pH of between 6 and 8. Suitable buffer substances for use in such buffered solutions include Tris, HEPES, MOPS and MES.

As used herein, the term "kit" refers to an article of manufacture comprising one or more containers and, optionally, a data carrier. Said one or more containers may be filled with one or more of the above mentioned means or reagents. Additional containers may be included in the kit that contain, e.g., diluents, buffers and further reagents. Said data carrier may be a non-electronic data carrier, e.g., a graphical data carrier such as an information leaflet, an information sheet, a bar code or an access code, or an electronic data carrier such as a floppy disk, a compact disk (CD), a digital versatile disk (DVD), a microchip or another semiconductor-based electronic data carrier. The access code may allow the access to a database, e.g., an interne database, a centralized, or a decentralized database. Said data carrier may comprise instructions for the use of the kit in the methods of the invention. In addition, the data carrier may comprise information or instructions on how to carry out the methods of the present invention.

The term "pharmaceutically active compound" (or "therapeutic agent"), as used herein, refers to any compound which has a positive or advantageous effect on the condition or disease state of a subject when administered to the subject in a therapeutically effective amount. Preferably, a pharmaceutically active compound has curative or palliative properties and may be administered to ameliorate, relieve, alleviate, reverse, delay onset of or lessen the severity of one or more symptoms of a disease or disorder. A pharmaceutically active compound may have prophylactic properties and may be used to delay the onset of a disease or to lessen the severity of such disease or pathological condition.

Pharmaceutically active compounds include pharmaceutically active peptides or proteins, pharmaceutically active nucleic acids, e.g., DNA or RNA, and other pharmaceutically active organic or inorganic molecules, e.g., small molecule compounds (i.e. bioactive organic compounds with a molecular weight of less than 900 Daltons).

The term "peptide", as used herein, comprises naturally or non-naturally occurring oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids (e.g., 10 to 100, 10 to 50, 10 to 40, 20 to 100, 20 to 50 or 20 to 40 amino acids) joined covalently by peptide bonds. The term "protein" preferentially refers to large peptides, preferably to peptides with more than 100 amino acid residues, but in general the terms "peptide" and "protein" are synonyms and are used interchangeably herein.

The term "pharmaceutically active peptide or protein" includes entire proteins or polypeptides, and can also refer to pharmaceutically active fragments thereof. It can also include pharmaceutically active analogs of a peptide or protein. The term "pharmaceutically active peptide or protein" further includes peptides and proteins that are antigens, i.e., administration of the peptide or protein to a subject elicits an immune response in a subject which may be therapeutic or partially or fully protective.

Examples of pharmaceutically active proteins include, but are not limited to, cytokines and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, immunoglobulins, soluble major histocompatibility complex antigens, immunologically active antigens such as bacterial, parasitic, or viral antigens, allergens, autoantigens, antibodies), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthetic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin III, glucocerebrosidase, erythropoietin granulocyte colony stimulating factor (GCSF) or modified Factor VIII, anticoagulants and the like.

In one embodiment, the pharmaceutically active protein according to the invention is a cytokine which is involved in regulating lymphoid homeostasis, preferably a cytokine which is involved in and preferably induces or enhances development, priming, expansion, differentiation and/or survival of T cells. In one embodiment, the cytokine is an interleukin. In one embodiment, the pharmaceutically active protein according to the invention is an interleukin selected from the group consisting of IL-2, IL-7, IL-12, IL-15, and IL-21.

The term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also downregulate other aspects of the immune response, for example shifting the immune response away from a TH2 immune response, which is useful for treating a wide range of TH2 mediated diseases. Immunologically active compounds can be useful as vaccine adjuvants.

A nucleic acid is according to the invention preferably deoxyribonucleic acid (DNA) or ribonucleic acid (RNA), more preferably RNA, most preferably in vitro transcribed RNA (IVT RNA) or synthetic RNA. Nucleic acids include according to the invention genomic DNA, cDNA, mRNA, recombinantly produced and chemically synthesized molecules. A nucleic acid may according to the invention be in the form of a molecule which is single stranded or double stranded and linear or closed covalently to form a circle.

Nucleic acids may also be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors: Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "DNA" relates to a molecule which comprises deoxyribonucleotide residues and preferably is entirely or substantially composed of deoxyribonucleotide residues. "Deoxyribonucleotide" relates to a nucleotide which lacks a hydroxyl group at the 2'-position of a β-D-ribofuranosyl group. The term "DNA" comprises isolated DNA such as partially or completely purified DNA, essentially pure DNA, synthetic DNA, and recombinantly generated DNA and includes modified DNA which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogs or analogs of naturally-occurring DNA.

In the context of the present invention, the term "RNA" relates to a molecule which comprises ribonucleotide residues and preferably is entirely or substantially composed of ribonucleotide residues. "Ribonucleotide" relates to a nucleotide with a hydroxyl group at the 2'-position of a β-D-ribofuranosyl group. The term "RNA" comprises isolated RNA such as partially or completely purified RNA, essentially pure RNA, synthetic RNA, and recombinantly generated RNA and includes modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

The term "pharmaceutically active nucleic acid" is meant to refer to nucleic acids having biological activities, such as protein expression, interference with gene expression, or immunostimulation. Such nucleic acids are, therefore, useful for interfering with gene expression (e.g., antisense RNA or siRNA), modifying protein activities (e.g., DNA aptamers or RNA aptamers) or activate immunity (e.g., isRNA or DNA vaccines or mRNA vaccines). A "pharmaceutically active nucleic" may also be a nucleic acid that encodes a pharmaceutically active peptide or protein or is pharmaceutically active on its own, e.g., it has one or more pharmaceutical activities such as those described for pharmaceutically active proteins.

According to the invention, the term "nucleic acid encoding a peptide or protein" means that the nucleic acid, if present in the appropriate environment, preferably within a cell, can direct the assembly of amino acids to produce the peptide or protein during the process of translation. Preferably, nucleic acids according to the invention are able to interact with the cellular translation machinery allowing translation of the peptide or protein.

In one embodiment, the nucleic acid is RNA.

According to the invention, "RNA" refers to single-stranded RNA or double stranded RNA and includes messenger RNA (mRNA), transfer RNA (tRNA), ribosomic RNA (rRNA), small nuclear RNA (snRNA), small inhibitory RNA (siRNA), small hairpin RNA (shRNA), microRNA (miRNA), antisense RNA, immunostimulating RNA (isRNA) and RNA aptamers. In a preferred embodiment, the RNA is selected from the group consisting of mRNA, siRNA, shRNA, miRNA, antisense RNA, isRNA and RNA aptamers.

The RNA may contain self-complementary sequences that allow parts of the RNA to fold and pair with itself to form double helices. According to the invention preferred as RNA are synthetic oligonucleotides of 6 to 100, preferably 10 to 50, in particular 15 to 30 or 15 to 20 nucleotides or messenger RNA (mRNA) of more than 50 nucleotides, preferably of 50 to 10,000, preferably 100 to 5000, in particular 200 to 3000 nucleotides.

According to the present invention, the term "messenger RNA (mRNA)" relates to a "transcript" which may be generated by using a DNA template and may encode a peptide or protein. Typically, an mRNA comprises a 5'-untranslated region, a protein coding region, and a 3'-untranslated region. In the context of the present invention, mRNA may be generated by in vitro transcription from a DNA template. The in vitro transcription methodology is known to the skilled person. For example, there is a variety of in vitro transcription kits commercially available.

According to the present invention, the term "small inhibitory RNA (siRNA)" relates to double stranded short (typically 19-23, preferably 21 nucleotides in length) oligonucleotides that can be used to induce the destruction of a target mRNA through the recognition of the target by one strand of the siRNA, a mechanism referred to as RNA interference (RNAi).

The term "small hairpin RNA (shRNA)" relates to a sequence of RNA that makes a tight hairpin turn and can be used to silence target gene expression via RNAi.

The terms "microRNA" or "miRNA" relate to a small non-coding RNA molecule (typically 19-25 nucleotides in length), which functions in transcriptional and post-transcriptional regulation of gene expression.

According to the present invention, the term "antisense RNA" relates to a single stranded RNA, usually a synthetic oligonucleotide that is designed to base-pair with a targeted cellular mRNA, thereby inhibiting physically the process of translation and eventually inducing destruction of the targeted mRNA.

According to the present invention, "immunostimulating RNA (isRNA)" relates to RNA that can activate innate immune receptors, such as, for example, the endoplasmic TLR-3, 7 and 8 or the cytosolic protein RIG-1. In one embodiment, the isRNA comprises one or more uridine (U) nucleotides.

According to the present invention, the term "RNA aptamer" relates to RNA that through its precise three dimensional structure can be used as an antibody, i.e., made to bind specifically to determined structures and thereby activate or block biological mechanisms.

According to the invention, the RNA may be modified. For example, RNA may be stabilized by one or more modifications having stabilizing effects on RNA.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or non-naturally occurring (synthetic) ribonucleotides in order to increase its stability and/or decrease cytotoxicity and/or modulate its immunostimulating potential. For example, in one embodiment, in the RNA used according to the invention uridine is substituted partially or completely, preferably completely, by pseudouridine.

In one embodiment, the term "modification" relates to providing a RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA if attached thereto, preferably in vivo and/or in a cell. Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be generated post-transcriptionally using capping enzymes, for example, capping enzymes of vaccinia virus.

The RNA may comprise further modifications. For example, a modification of mRNA used in the present invention may be an extension or truncation of the naturally occurring poly(A) tail.

The term "stability" of RNA relates to the "half-life" of RNA. "Half-life" relates to the period of time which is needed to eliminate half of the activity, amount, or number of molecules. In the context of the present invention, the half-life of a RNA is indicative for the stability of said RNA.

If, according to the present invention, it is desired to decrease stability of RNA, it is also possible to modify RNA so as to interfere with the function of elements as described above increasing the stability of RNA.

According to the present invention, RNA may be obtained by chemical synthesis or by in vitro transcription of an appropriate DNA template. In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". The promoter for controlling transcription can be any promoter for any RNA polymerase. Particular examples of RNA polymerases are the T7, T3, and SP6 RNA polymerases. A DNA template for in vitro transcription may be obtained by cloning of a nucleic acid, in particular cDNA, and introducing it into an appropriate vector for in vitro transcription. The cDNA may be obtained by reverse transcription of RNA. Preferably, cloning vectors are used for producing transcripts which generally are designated transcription vectors.

The term "translation" according to the invention relates to the process in the ribosomes of a cell by which a strand of messenger RNA directs the assembly of a sequence of amino acids to make a peptide or protein.

The term "inhibition of gene expression" relates to a process, wherein RNA oligonucleotides (e.g., single stranded antisense or double stranded siRNA) can be used to bind specific mRNA sequences inducing either the degradation of the targeted mRNA and/or to the blockade of translation.

In one embodiment the pharmaceutically active compound is an antigen or a nucleic acid encoding an antigen or a fragment thereof, e.g., a disease-associated antigen.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases.

According to the invention, the term "disease" also refers to cancer diseases. The terms "cancer disease" or "cancer" (medical term: malignant neoplasm) refer to a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor, i.e. a swelling or lesion formed by an abnormal growth of cells (called neoplastic cells or tumor cells), but some, like leukemia, do not. Examples of cancers include, but are not limited to, carcinoma, lymphoma, blastoma, sarcoma, glioma and leukemia. More particularly, examples of such cancers include bone cancer, blood cancer, lung cancer, liver cancer, pancreatic cancer, skin cancer, cancer of the head or neck, cutaneous or intraocular malignant melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases.

Malignant melanoma is a serious type of skin cancer. It is due to uncontrolled growth of pigment cells, called melanocytes.

According to the invention, a "carcinoma" is a malignant tumor derived from epithelial cells. This group represents the most common cancers, including the common forms of breast, prostate, lung and colon cancer.

Lymphoma and leukemia are malignancies derived from hematopoietic (blood-forming) cells.

A sarcoma is a cancer that arises from transformed cells in one of a number of tissues that develop from embryonic mesoderm. Thus, sarcomas include tumors of hone, cartilage, fat, muscle, vascular, and hematopoietic tissues.

Blastic tumor or blastoma is a tumor (usually malignant) which resembles an immature or embryonic tissue. Many of these tumors are most common in children.

A glioma is a type of tumor that starts in the brain or spine. It is called a glioma because it arises from glial cells. The most common site of gliomas is the brain.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The term "infectious disease" refers to any disease which can be transmitted from individual to individual or from organism to organism, and is caused by a microbial agent (e.g. common cold). Examples of infectious diseases include viral infectious diseases, such as AIDS (HIV), hepatitis A, B or C, herpes, herpes zoster (chicken-pox), German measles (rubella virus), yellow fever, dengue etc. flaviviruses, influenza viruses, hemorrhagic infectious diseases (Marburg or Ebola viruses), and severe acute respiratory syndrome (SARS), bacterial infectious diseases, such as Legionnaire's disease (*Legionella*), sexually transmitted diseases (e.g. chlamydia or gonorrhea), gastric ulcer (*Helicobacter*), cholera (*Vibrio*), tuberculosis, diphtheria, infections by *E. coli*, *Staphylococci*, *Salmonella* or *Streptococci* (tetanus); infections by protozoan pathogens such as malaria, sleeping sickness, leishmaniasis; toxoplasmosis, i.e. infections by Plasmodium, Trypanosoma, Leishmania and Toxoplasma; or fungal infections, which are caused e.g. by *Cryptococcus neoformans, Histoplasma capsulatum, Coccidioides immitis, Blastomyces dermatitidis* or *Candida albicans*.

The term "autoimmune disease" refers to any disease in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

The term "antigen" relates to an agent comprising an epitope against which an immune response is to be generated. The term "antigen" includes in particular proteins, peptides, polysaccharides, nucleic acids, especially RNA and DNA, and nucleotides. The term "antigen" also includes agents, which become antigenic—and sensitizing—only through transformation (e.g. intermediately in the molecule or by completion with body protein). An antigen is preferably presentable by cells of the immune system such as antigen presenting cells like dendritic cells or macrophages. In addition, an antigen or a processing product thereof is preferably recognizable by a T or B cell receptor, or by an immunoglobulin molecule such as an antibody. In a preferred embodiment, the antigen is a disease-associated antigen, such as a tumor-associated antigen, a viral antigen, or a bacterial antigen.

The term "disease-associated antigen" is used in it broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen may therefore be used for therapeutic purposes. Disease-associated antigens are preferably associated with infection by microbes, typically microbial antigens, or associated with cancer, typically tumors.

The term "disease involving an antigen" refers to any disease which implicates an antigen, e.g. a disease which is characterized by the presence of an antigen. The disease involving an antigen can be an infectious disease, an autoimmune disease, or a cancer disease or simply cancer. As mentioned above, the antigen may be a disease-associated antigen, such as a tumor-associated antigen, a viral antigen, or a bacterial antigen.

In one embodiment, a disease-associated antigen is a tumor-associated antigen. Preferably, the diseased organ or tissue is characterized by diseased cells such as cancer cells expressing a disease-associated antigen and/or being characterized by association of a disease-associated antigen with their surface. Immunization with intact or substantially intact tumor-associated antigens or fragments thereof such as MHC class I and class II peptides or nucleic acids, in particular mRNA, encoding such antigen or fragment makes it possible to elicit a MHC class I and/or a class II type response and, thus, stimulate T cells such as CD8+ cytotoxic T lymphocytes which are capable of lysing cancer cells and/or CD4+ T cells. Such immunization may also elicit a humoral immune response (B cell response) resulting in the production of antibodies against the tumor-associated antigen. Furthermore, antigen presenting cells (APC) such as dendritic cells (DCs) can be loaded with MHC class I—presented peptides by transfection with nucleic acids encoding tumor antigens in vitro and administered to a patient. In one embodiment, the term "tumor-associated antigen" refers to a constituent of cancer cells which may be derived from the cytoplasm, the cell surface and the cell nucleus. In particular, it refers to those antigens which are produced, preferably in large quantity, intracellularly or as surface antigens on tumor cells. Examples for tumor antigens include HER2, EGFR, VEGF, CAMPATHI-antigen, CD22, CA-125, HLA-DR, Hodgkin-lymphoma or mucin-1, but are not limited thereto.

According to the present invention, a tumor-associated antigen preferably comprises any antigen which is characteristic for tumors or cancers as well as for tumor or cancer cells with respect to type and/or expression level. In one embodiment, the term "tumor-associated antigen" relates to proteins that are under normal conditions, i.e. in a healthy subject, specifically expressed in a limited number of organs and/or tissues or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2 or 1. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably not or only rarely expressed in normal tissues or is mutated in tumor cells. Preferably, the tumor-associated antigen or the aberrant expression of the tumor-associated antigen identifies cancer cells. In the context of the present invention, the tumor-associated antigen that is expressed by a cancer cell in a subject, e.g., a patient suffering from a cancer disease, is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, a tumor-associated antigen is presented in the context of MHC molecules by a cancer cell in which it is expressed.

Examples for differentiation antigens which ideally fulfill the criteria for tumor-associated antigens as contemplated by the present invention as target structures in tumor immunotherapy, in particular, in tumor vaccination are the cell surface proteins of the Claudin family, such as CLDN6 and CLDN18.2. These differentiation antigens are expressed in tumors of various origins, and are particularly suited as target structures in connection with antibody-mediated cancer immunotherapy due to their selective expression (no expression in a toxicity relevant normal tissue) and localization to the plasma membrane.

Further examples for antigens that may be useful in the present invention are p53, ART-4, BAGE, beta-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pml/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term "immune response", as used herein, relates to a reaction of the immune system such as to immunogenic organisms, such as bacteria or viruses, cells or substances. The term "immune response" includes the innate immune response and the adaptive immune response. Preferably, the immune response is related to an activation of immune cells, an induction of cytokine biosynthesis and/or antibody production.

According to the present invention, the term "treatment of a disease" includes curing, shortening the duration, ameliorating, slowing down or inhibiting progression or worsening of a disease or the symptoms thereof.

The term "immunotherapy" relates to a treatment preferably involving a specific immune reaction and/or immune effector function(s).

The term "immunization" or "vaccination" describes the process of treating a subject for therapeutic or prophylactic reasons.

The term "subject", as used herein, preferably relates to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity, such as animals of zoos. In a preferred embodiment, the subject is a human.

The present invention also provides a method of preparing a pharmaceutical composition, the method comprising
  providing an aqueous formulation as defined above; and
  mixing the aqueous formulation with a pharmaceutically active compound.

In one embodiment, the pharmaceutically active compound comprises a nucleic acid, wherein, preferably, the nucleic acid is provided in a buffered solution having a pH of between 6 and 8.

The present invention also provides a pharmaceutical composition prepared by the method as defined above.

In one embodiment, the pharmaceutical composition comprises liposomes loaded with the pharmaceutically active compound.

In one embodiment, the pharmaceutical composition comprises nucleic acid lipoplexes.

The terms "nucleic acid lipoplex" or "lipoplex", as used herein, refer to a complex of lipids and nucleic acids, such as DNA or RNA, preferably RNA. Lipoplexes are formed spontaneously when cationic lipids (e.g., in the form of cationic liposomes, which often also include neutral helper lipids), cationic polymers and other substances with positive charges are mixed with nucleic acids, and have been shown to deliver nucleic acids into cells. In one embodiment, the lipoplexes have an average diameter in the range of from about 50 nm to about 1000 nm, preferably from about 100 nm to about 800 nm, preferably about 200 nm to about 600 nm, such as about 300 nm to about 500 nm.

The average "diameter" or "size" of the lipid-based particles (e.g., liposomes or lipoplexes) described herein is generally the "design size" or intended size of the lipid-based particles prepared according to an established process. Size may be a directly measured dimension, such as average or maximum diameter, or may be determined by an indirect assay such as a filtration screening assay. Direct measurement of particle size is typically carried out by dynamic light scattering. Frequently, the results from dynamic light scattering measurements are expressed in terms of $Z_{average}$ (a measure for the average size) and the polydispersity index, PI or PDI (a measure for the polydispersity). As minor variations in size arise during the manufacturing process, a variation up to 40% of the stated measurement is acceptable and considered to be within the stated size. Alternatively, size may be determined by filtration screening assays. For example, a particle preparation is less than a stated size, if at least 97% of the particles pass through a "screen-type" filter of the stated size.

In one embodiment, the at least one pH adjusting agent is associated with the liposomes and/or lipoplexes.

The pharmaceutical compositions of the invention are preferably sterile and contain an effective amount of lipids or lipid-based particles (e.g., liposomes or lipoplexes). The pharmaceutically compositions may also comprise further agents as discussed herein, such as an additional therapeutic agent or antigen. The pharmaceutical compositions of the invention may further comprise one or more pharmaceutically acceptable carriers, diluents and/or excipients. The pharmaceutical composition of the invention may further comprise at least one adjuvant.

An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. An effective amount will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered may depend on various of such parameters. In the case that a reaction in a patient is insufficient with an initial dose, higher doses (or effectively higher doses achieved by a different, more localized route of administration) may be used.

The pharmaceutical compositions described herein may be administered via any conventional route. In one embodiment, the pharmaceutical composition is formulated for systemic administration. According to the present invention, systemic administration is preferably by parenteral administration including by injection or infusion, e.g., intravenously, intraarterially, subcutaneously, in the lymph node, intradermally or intramuscularly.

Compositions suitable for parenteral administration usually comprise a sterile aqueous or non-aqueous preparation of the active compound, which is preferably isotonic to the blood of the recipient. Examples of compatible carriers and diluents/solvents are sterile water (e.g., water-for-injection), Ringer solution and isotonic sodium chloride solution. In addition, usually sterile, fixed oils are used as solution or suspension medium.

The term "pharmaceutically acceptable", as used herein, refers to the non-toxicity of a material which, preferably, does not interact with the action of the active component of the pharmaceutical composition.

The Willi "excipient" when used herein is intended to indicate all substances which may be present in a pharmaceutical composition of the present invention and which are not active ingredients such as, e.g., carriers, binders, lubricants, thickeners, surface active agents, preservatives, emulsifiers, buffers, flavoring agents, or colorants.

The term "adjuvant" relates to compounds which prolong or enhance or accelerate an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances, as explained above, are to be considered. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, INFα, INF-γ, GM-CSF, LT-α, or growth factors, e.g. hGH. Further known adjuvants are aluminium hydroxide, Freund's adjuvant or oil such as Montanide, most preferred Montanide® ISA51. Lipopeptides, such as Pam3Cys, are also suitable for use as adjuvants in the pharmaceutical compositions of the present invention.

The pharmaceutical compositions of the present invention can also be used in conjunction with another therapeutic agent which can be administered prior to, simultaneously with or after administration of the pharmaceutical compositions of the present invention. Such therapeutic agents include immunomodulating agents, which may be immunostimulating or immunosuppressive, chemotherapeutic drugs for cancer patients, e.g. gemcitabine, etopophos, cis-platin, carbo-platin, antiviral agents, anti-parasite agents or an anti-bacterial agents and, if administered simultaneously may be present in a pharmaceutical composition of the present invention.

The pharmaceutical composition of the invention may be used for inducing an immune response, in particular an immune response against a disease-associated antigen or cells expressing a disease-associated antigen, such as an immune response against cancer. Accordingly, the pharmaceutical composition may be used for prophylactic and/or therapeutic treatment of a disease involving a disease-associated antigen or cells expressing a disease-associated antigen, such as cancer. Preferably said immune response is a T cell response. In one embodiment, the disease-associated antigen is a tumor antigen.

The present invention also provides a pharmaceutical composition or kit as defined herein for use in a method of treatment or prevention of a disease or for use in a method of immunostimulation.

The present invention also relates to the use of a pharmaceutical composition or kit as defined herein in the manufacture of a medicament for the treatment or prevention of a disease or for use in a method of immunostimulation.

The present invention further provides a method of treatment or prevention of a disease or to a method of immunostimulation, the methods comprising the step of administering a pharmaceutical composition as defined herein to a subject in need thereof.

Finally, the present invention provides a method of chemically stabilizing an aqueous formulation comprising at least one lipid having one or more bonds selected from the group consisting of ester bonds, thioester bonds and amide bonds, preferably ester bonds, the method comprising
adjusting the pH of the aqueous formulation to a pH of between 2 and 5.5.

In one embodiment, the chemical stabilization occurs by inhibition of ester bond, thioester bond and/or amid bond hydrolysis, preferably ester bond hydrolysis.

In one embodiment, at least one of the lipids present in the aqueous formulation is a cationic lipid, preferably a cationic lipid as defined herein.

In one embodiment, the overall net charge of the lipids present in the aqueous formulation is positive.

In one embodiment, the pH is adjusted to a pH of between 2 and 5, preferably of between 2.5 and 5, more preferably of between 3 and 4.5, more preferably of between 3 and 4, and even more preferably of between 3.5 and 4. In a further preferred embodiment, the aqueous formulation has a pH of between 3.1 and 3.9.

In one embodiment, the pH of the aqueous lipid formulation is adjusted by adding at least one pH adjusting agent, preferably at least one pH adjusting agent as defined above.

In one embodiment, the at least one lipid having one or more bonds selected from the group consisting of ester bonds, thioester bonds and amide bonds is as defined above.

In one embodiment, the lipids present in the aqueous formulation form liposomes.

In one embodiment, the at least one pH adjusting agent is associated with the liposomes. The present invention is further illustrated by the following examples which are not to be construed as limiting the scope of the invention.

Examples

Materials
(R)-N,N,N-trimethyl-2,3-dioleyloxy-1-1propanaminum chloride (R-DOTMA), Merck & Cie.
1,2-dioleoyl-sn-glycero-3-phosphoethanolamine (DOPE), Corden Pharma
Ethanol 99.5% Ph. Eur., Carl Roth
Acetic acid United States Pharmacopeia (USP), AppliChem
Sodium acetate USP, AppliChem
HEPES buffer, Life Technologies
Water-for-injection, Baxter
1 mL Syringe inject-F, B. Braun
0.9×40 mm needle Microlance 3, BD
R6 Glass type I vials, Wheaton
20 mm Aluminum seals, Wheaton
20 mm Butyl Stoppers, Wheaton Example 1

Preparation of Liposomes

All materials in contact with the solutions and liposome preparations were sterile and disposable. Liposomes were formed with the so-called ethanol injection technique (Batzri and Korn, 1973), where lipids dissolved in ethanol are injected into an aqueous phase under stirring.

The lipid ratios and lipid concentrations in ethanol varied depending on the desired formulation and particle size. For DOTMA/DOPE liposomes, the ethanol solution contained DOTMA and DOPE in a molar ratio of 2:1 at a total lipid concentration of about 330 mM. For DOTAP/DOPE liposomes, the ethanol solution contained DOTAP and DOPE in a molar ratio of 2:1 at a total lipid concentration of about 330 mM. The solutions were sterilized by filtration through a filter of 0.2 μm pore size (Millipore Millex MP).

The sterile lipid solutions in ethanol were then injected into a disposable spinner flask containing an aqueous phase and stirred at a rate of 150 rpm for at least one hour. The aqueous phase was either water-for-injection (wfi) or Milli-Q-filtered water with a conductivity of 1.3 μS/cm at 25° C., or it was a buffer solution made up from buffer salts and acids as indicated. All materials were of pharmaceutical grade. Injection was performed up to a final lipid concentration of 5-10 mM, depending on the experiment. Most experiments were performed at 6.6 mM final total lipid concentration in the aqueous phase.

The resulting liposome preparations were filtered through a cellulose acetate filter of 0.45 μm pore size. The filtrate preparation was then diluted with dispersion solution to the desired concentration and stored in bioprocess bags. For standard experiments, 4 mM was selected as a final concentration. Storage temperature prior to the pH stability experiments was 2-5° C.

Example 2

Stability of DOTMA/DOPE Liposomes as a Function of the pH Value

The stability of DOPE in DOTMA/DOPE liposomes was investigated after adjusting the pH to different values between pH 7 and pH 4. For pH 7, 10 mM HEPES buffer was used. For all lower pH values, acetic acid buffers (all 10 mM) were used (see Table 1). R6 glass type I vials were filled with 2 mL of the liposomes dispersion and stored in a stability chamber at 37° C. pH values were measured by potentiometry using a WTW pH-meter inoLab pH 7310, Weilheim, Germany.

TABLE 1

| Dispersion solutions | | |
|---|---|---|
| Solution | Concentration | pH |
| USP Acetate Buffer | 10 mM | 4 |
| USP Acetate Buffer | 10 mM | 5 |
| USP Acetate Buffer | 10 mM | 6 |
| HEPES | 10 mM | 7 |

The lipid stability was tested at different time points up to 6 weeks after preparation of the liposomes by measuring the lipid concentration in the liposome preparation using a HPLC system (Agilent Technologies 1200 equipped with DAD and ELSD detectors, Santa Clara, CA, USA).

Results are given in FIG. 1. Plotted is the normalized recovery of DOPE (in percent) from the DOTMA/DOPE liposomes. Only DOPE is shown, as for DOTMA, under all conditions, no indication for degradation was found, which is due to the fact that DOTMA comprises ether bonds instead of ester bonds. The liposomes in the aqueous phase with the lowest pH, pH 4, showed the best stability with no significant degradation after 6 weeks. In contrast, at pH 5, already degradation with a recovery of only 80% of the initial value was observed. The stability decreased with increasing pH, and the highest degradation was found for pH 6 and pH 7 (the range, where best stability would be expected).

Example 3

Influence of Buffer Concentration on Liposome Stability

The stability of DOPE in DOTMA/DOPE liposomes (DOTMA:DOPE at a 2:1 molar ratio) in the low pH range was further investigated. In this experiment, even lower pH values were tested by adding pure acetic acid (10 mM). The acetic acid buffers were added at three different concentrations, namely 1 mM, 5 mM and 10 mM. The samples were stressed at 40° C. for 5 weeks.

Figure 2:
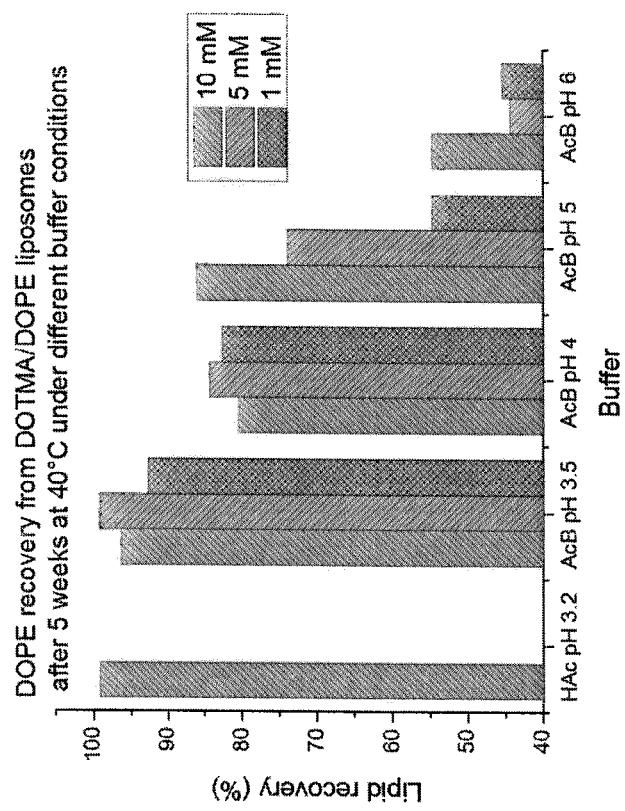
FIG. 2 shows the percentage of DOPE recovered from DOTMA/DOPE liposome dispersions with different pH values prepared in the presence of acetic acid (HAc) or various concentrations of acetic acid buffers (AcB). The dispersion were stored for 5 weeks at 40° C.

In FIG. 2, the recovery of DOPE is given for the various conditions. In confirmation of the results from the experiment described in Example 2 (FIG. 1), the stability was continuously improved by lowering the pH. Pure acetic acid (10 mM; pH 3.2) appeared to be at least as good or better than pH 3.5 acetate buffer (AcB) at the same concentration. The stabilizing effect of the acidic buffers was concentration dependent, as can be most clearly seen at pH 5 and 6. As a trend, higher buffer concentrations resulted in better protection from hydrolysis. At very low pH values this effect was less pronounced. It can be concluded that addition of pure acetic acid to a suitable concentration can be a simple and straightforward way to obtain stabilization of DOPE with respect to ester hydrolysis.

Example 4

Comparison of the Results of Different Stress Studies

Figure 3:
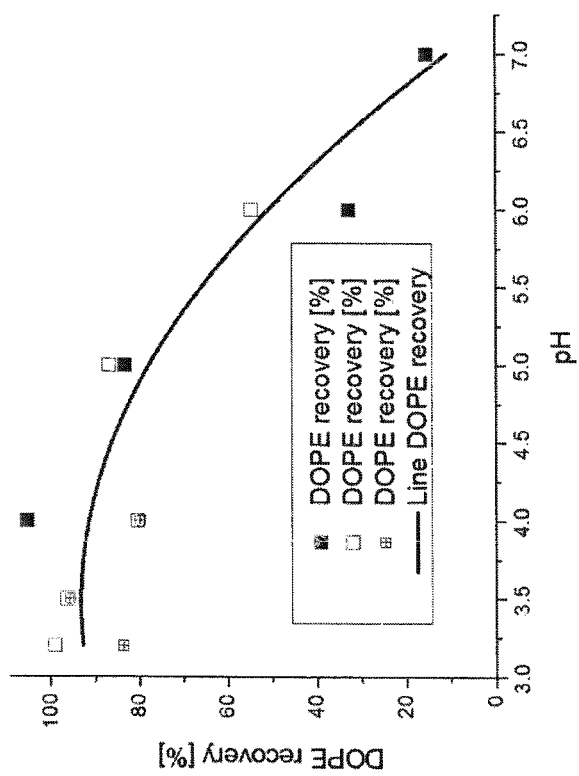
FIG. 3 shows the percentage of DOPE recovered from stressed DOTMA/DOPE liposome dispersions after 5 or 6 weeks as a function of the pH value. Results from 3 independent experiments are shown.

In FIG. 3, the outcome of several independent stress studies is summarized. In each case, DOTMA/DOPE liposomes were stressed in acetic acid and acetic acid buffer solutions (all 10 mM) at different pH values at 40° C. Results after 5 or 6 weeks are shown (squares with different fillings). The solid line was drawn in order to visualize the general trend.

A correlation between lipid stability and pH value can be readily recognized. Maximum stability is obtained in the pH range below 4, where the protective effect appears to reach a plateau. Lower pH values or higher buffer/acid concentrations may lead to even better protection from hydrolysis. However, in the present context, extremely high buffer concentrations or extremely low pH values are not desirable, because such harsh conditions may not be used in formulations for administration to patients.

Example 5

Stability of DOTAP/DOPE Liposomes as a Function of the pH Value

In this study, the stability of liposomes with DOTAP instead of DOTMA was investigated. DOTAP is a cationic lipid with a similar structure as DOTMA, but comprises ester bonds instead of ether bonds. Therefore, DOTAP should be prone to ester hydrolysis in a similar way as DOPE. Besides the change from DOTMA to DOTAP, all other conditions remained unchanged.

Figure 4:
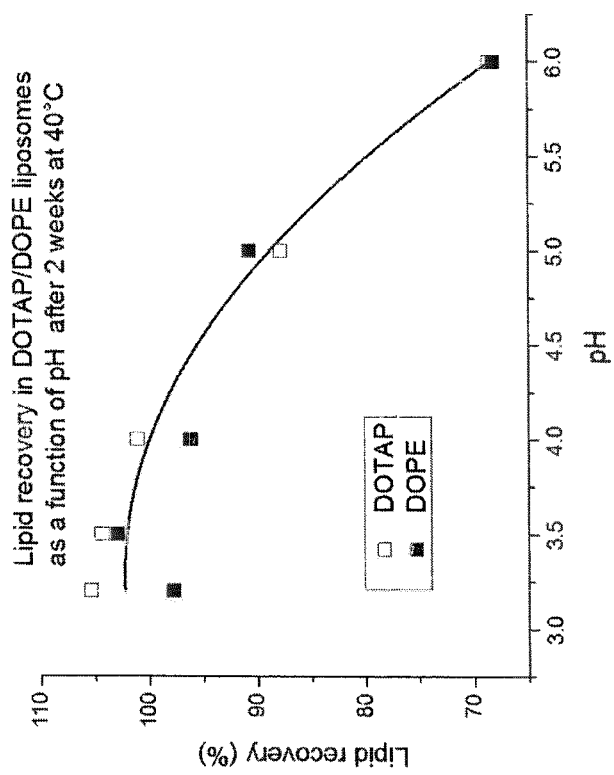
FIG. 4 shows the percentage of lipid recovery from DOTAP/DOPE liposomes after 2 weeks at 40° C. as a function of the pH value.

In FIG. 4, the results from lipid recovery measurements after two weeks at 40° C. are shown for different pH conditions in the aqueous phase. The results for both DOTAP and DOPE are shown. For both lipids hydrolysis took place, wherein the general behavior was equivalent and similar to the finding for DOPE in DOTMA/DOPE liposomes. Thus, the hydrolysis of DOTAP could be prevented in the same way as for DOPE by the addition of acidic buffers or acids, such as acetic acid.

Example 6

Figure 5:
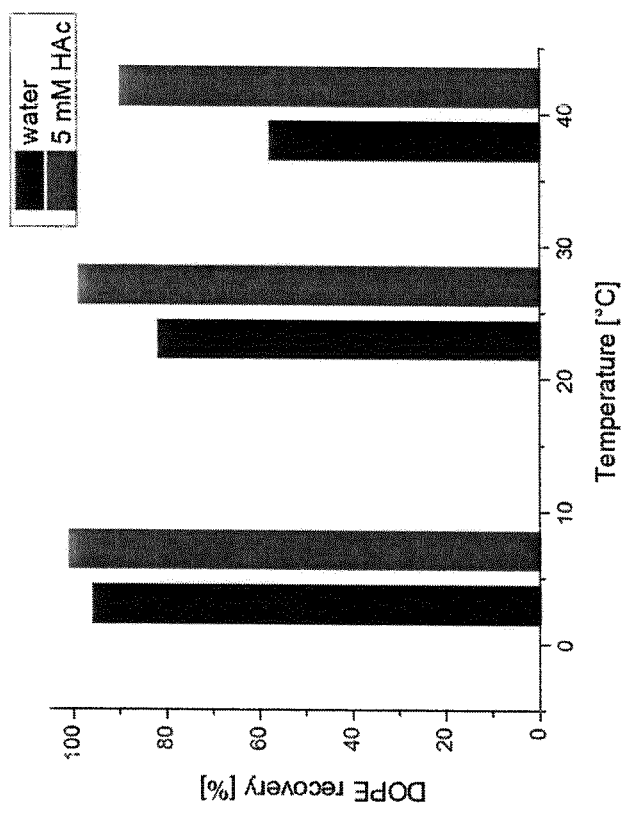
FIG. 5 shows the percentage of DOPE recovery from DOTMA/DOPE liposomes in water-for-injection with our without 5 mM acetic acid (HAc) after storage for 3 months at 5° C., 25° C. or 40° C.

Comparison of DOPE Degradation in DOTMA/DOPE Liposomes in Water-for-Injection With or Without 5 mM Acetic Acid Addition of acetic acid was tested for stabilization of liposomes for pharmaceutical use, which had been previously manufactured in pure water-for-injection (wfi). In FIG. 5, the results from stress studies with and without acetic acid are shown. For the stabilized liposomes, 5 mM acetic acid was added to the aqueous phase prior to liposome formation. Results from DOPE recovery measurements after 3 months storage at three different temperatures, 5° C., 25° C. and 40° C., are shown. In all three cases, the recovery was higher with the acetic acid present in the aqueous phase. The effect became more pronounced at higher temperatures (stress conditions) and were most clearly visible at 40° C., where recovery could be improved from about 60% to about 90%.

When comparing the stability at different temperatures, addition of 5 mM acetic acid had a similar effect as lowering the storage temperature by 15 to 35° C. Considering the rule of thumb that lowering the temperature by 10° C. leads to a decrease of the hydrolysis rate by a factor of two, this would correspond to an increase in stability (or decrease of the hydrolysis rate) at a given temperature by a factor of about 4 (taking an effect equivalent to a decrease in temperature of 20° C. as a basis).

Example 7

Lipoplex Formation pH-stabilized DOTMA/DOPE liposomes were used to form RNA lipoplex formulations for intravenous injection with equivalent or better quality with respect to physicochemical characteristics in comparison to lipoplexes made from liposomes that were not pH-stabilized.

RNA lipoplexes were prepared according to the following protocol:
1. Addition of 4 mL 0.9% NaCl solution to 1.1 mL RNA;
2. Addition of 0.4 mL liposomes to the RNA/NaCl mixture; and
3. Equilibration for 3 minutes at room temperature In Table 2, the results of the physicochemical characterization of liposomes and lipoplexes are shown. The liposome diameter was measured by dynamic light scattering using a PSS-Nicomp 380 ZLS, Santa Barbara, CA, USA. While the size and the polydispersity index (PDI) of the liposomes with acetic acid were somewhat smaller than those without acetic acid, the particle size of the lipoplexes was somewhat larger with than without acetic acid, whereas the polydispersity index was smaller. The larger size is considered favorable in terms of biological activity, while the smaller polydispersity index is favorable with respect quality requirements. The number of sub-visible particles, which must not be present in injectable products above certain thresholds, was significantly lower when stabilized liposomes were used for the preparation of lipoplexes. The pH value of the final formulation was above 6 and therefore well-suited for injection. The osmolarity was equivalent to physiological conditions.

TABLE 2

Physicochemical characterization of liposomes and RNA lipoplexes

| Aqueous phase In liposomes | Liposomes | | RNA-Lipoplexes | | | | |
|---|---|---|---|---|---|---|---|
| | Particle size nm | PDI | Particle size nm | PDI | SVP-USP 778 >10 µm | >25 µm | pH | Osmolarity mOsmol/Kg |
| wfi | 410 | 0.26 | 468 | 0.256 | 1150 | 45 | 6.9 | 301 |
| 5 mM HAc in wfi | 329 | 0.239 | 553 | 0.226 | 517 | 12 | 6.1 | 304 |

Example 8

Biological Evaluation of Lipoplexes

The biological activity of the lipoplexes formed from pH-stabilized liposomes (addition of acetic acid) was investigated by bioluminescence measurements. Uptake and translation of formulated firefly luciferase-encoding RNA (luc RNA lipoplexes) were evaluated by in vivo bioluminescence imaging using the Xenogen IVIS Spectrum imaging system (Caliper Life Sciences). Briefly, an aqueous solution of D-luciferin (75 mg/kg body weight) (Caliper Life Sciences) was injected in mice i.p. 6 h after administration of 20 µg luc RNA lipoplexes. Emitted photons of live animals or extracted tissues were quantified 10 min later with an exposure time of 1 min. Regions of interest (ROI) from the displayed images were drawn and bioluminescence was quantified as average radiance (photons/sec/cm2/sr, represented by color bars) using IVIS Living Image 4.0 Software.

Figure 6:
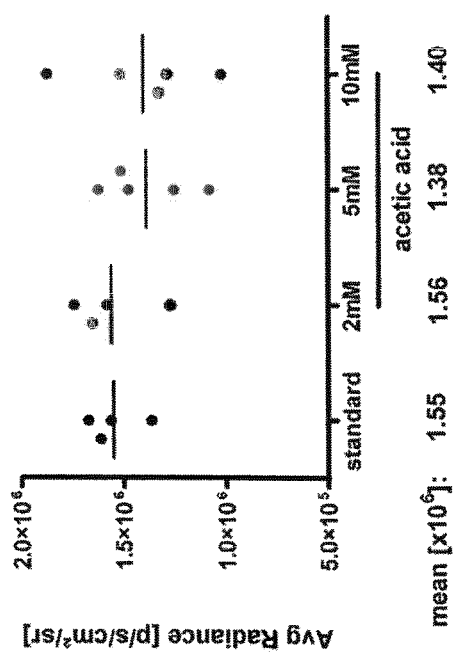
FIG. 6 shows the bioluminescence signals in mice injected with luciferase-encoding RNA lipoplexes prepared with pH-stabilized liposomes or non-pH-stabilized liposomes (standard).

As shown in FIG. 6, the signals obtained with lipoplexes formed from pH-stabilized liposomes (see Table 3) were only slightly lower than those with lipoplexes formed from non-pH-stabilized liposomes. The very small decrease of the absolute number was lower than the margin of error of the measurements and therefore not significant.

TABLE 3 pH values of lipoplex samples

| Sample | pH |
|---|---|
| Reference liposomes | 6.9 |
| 10 mM acetic acid liposomes | 5.0 |
| 5 mM acetic acid liposomes | 6.0 |
| 2 mM acetic acid liposomes | 6.7 |

Example 9

Stability of DOPE in DOTMA/DOPE Liposomes Prepared Under GMP or GMP-Like Conditions in Water-for-Injection or Water-for-Injection Comprising 5 mM Acetic Acid Liposomes consisting of DOTMA/DOPE in a 2/1 molar ratio were manufactured by the ethanol injection technique to a concentration of about 4 mM (total lipid). As aqueous phase, either water-for-injection (wfi) or wfi comprising 5 mM acetic acid was used. Liposomes in wfi were referred to as L1 liposomes, liposomes in wfi comprising 5 mM acetic acid (resulting in a pH value between 3 and 4) were referred to as L2 liposomes. Besides the presence or absence of acetic acid, all other manufacturing conditions were identical. GMP grade lipids were used, and manufacturing was performed under GMP or GMP-like conditions. Several batches of L1 and L2 liposomes were manufactured, and, after to glass vials, stability was tested at the following temperatures:
1. 5° C. (2-8° C.);
2. 25° C. (22-28° C.)=accelerated conditions;
3. 40° C. (38-42° C.)=stress conditions.

Figure 7:
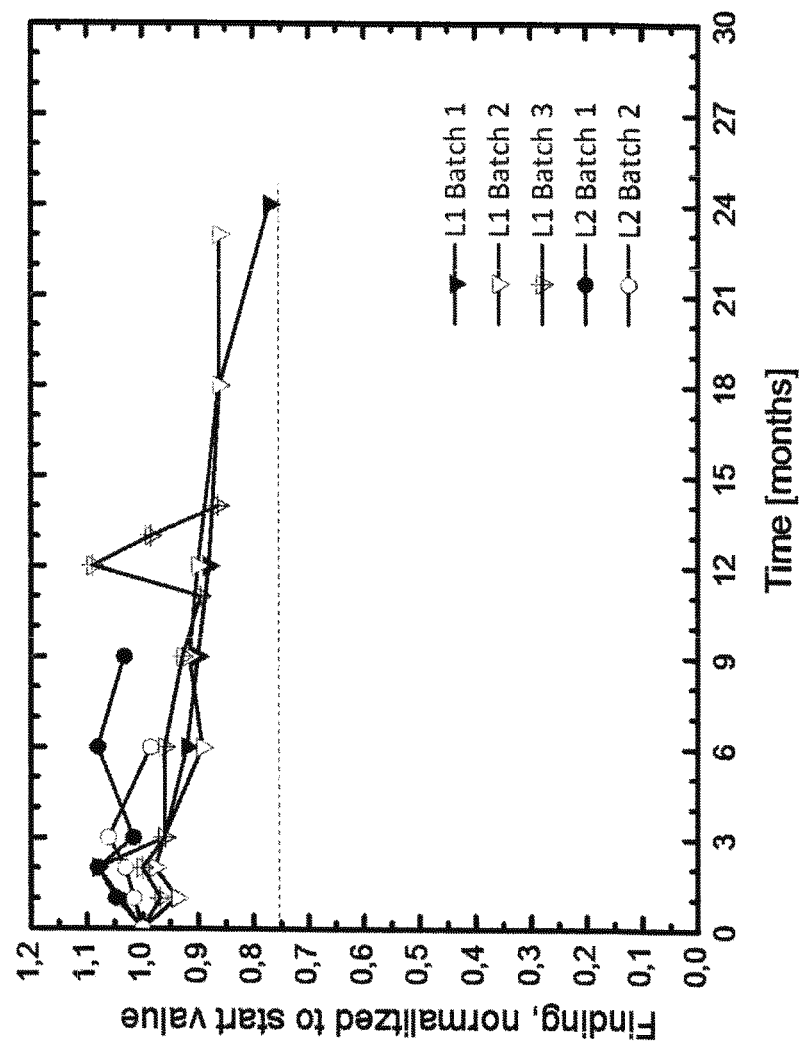
FIG. 7 shows the stability of DOPE in DOTMA/DOPE liposomes in water-for-injection (L1) or in water-for-injection with 5 mM acetic acid (L2) at 5° C. (A), 25° C. (B) or 40° C. (C). Liposomes were prepared under GMP or GMP-like conditions.
Figure 7:
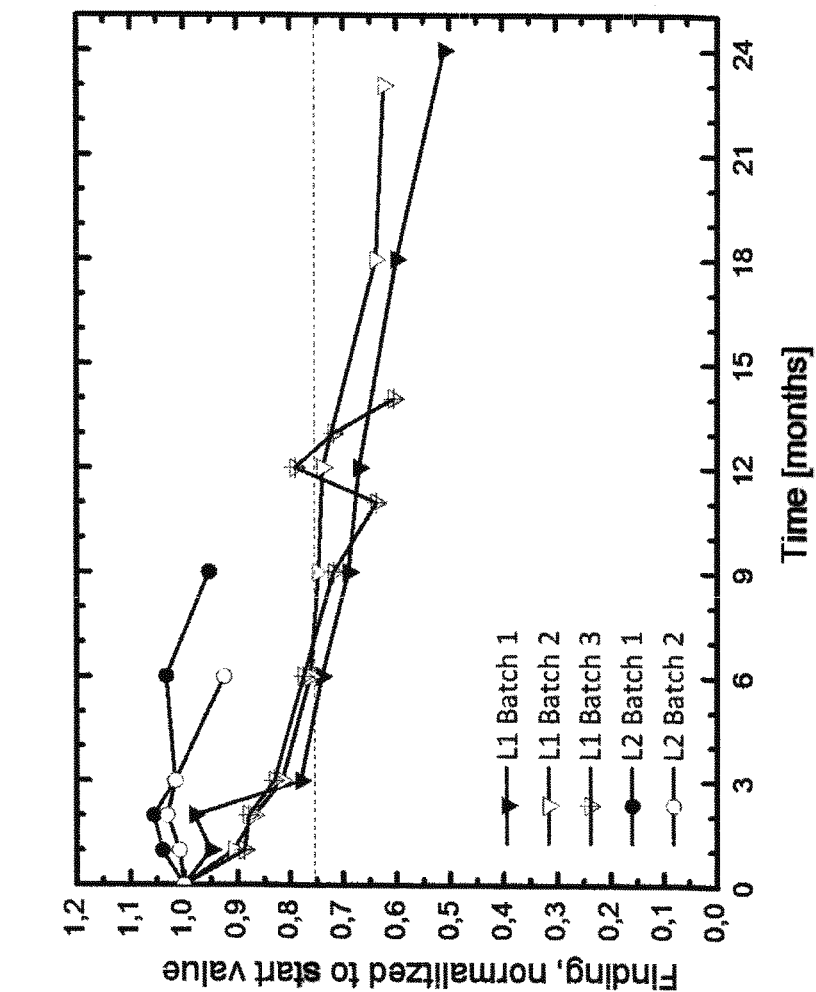
Figure 7:
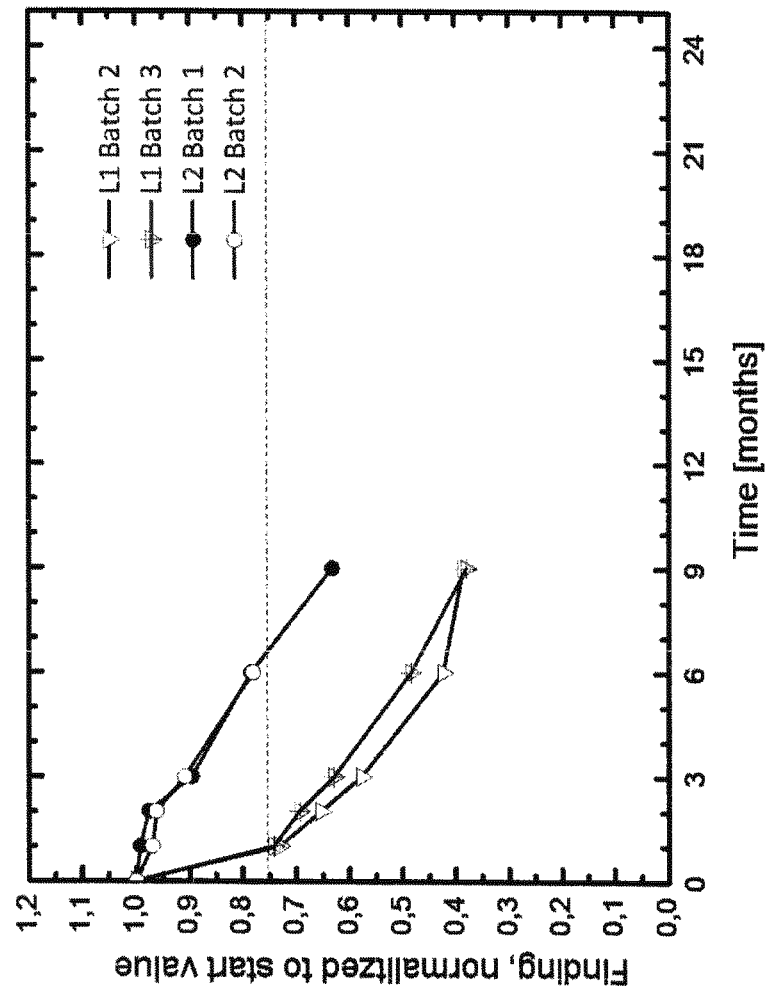

Stability data for L1 and L2 liposomes were collected over a period of up to 25 months (L1) and up to 9 months (L2), respectively. The stability studies are still ongoing. In FIGS. 7 A to C, stability data for different batches of L1 and L2 liposomes at different temperatures are shown. Under all temperature conditions and for all manufactured batches the stability of DOPE In L2 liposomes was substantially better than that in L1 liposomes.

This indicates that pH adjustment to acidic conditions by addition of 5 mM acetic acid to the aqueous phase significantly improves the stability of DOPE in the liposomes. The shelf-life of the liposomes can be increased by an approximate factor of 4.

REFERENCES

Batzri, S. and E. D. Korn (1973). "Single bilayer liposomes prepared without sonication." Biochim Biophys Acta 298 (4): 1015-1019.
Chen, C. J., D. D. Han, C. F. Cai and X. Tang (2010). "An overview of liposome lyophilization and its future potential." Journal of Controlled Release 142(3): 299-311.
Stark, B., G. Pabst and R. Prassl (2010). "Long-term stability of sterically stabilized liposomes by freezing and freeze-drying: Effects of cryoprotectants on structure." European Journal of Pharmaceutical Sciences 41(3-4): 546-555.
van Winden, E. C. and D. J. Crommelin (1999). "Short term stability of freeze-dried, lyoprotected liposomes." J Control Release 58(1): 69-86.

The invention claimed is:

1. An aqueous liposome dispersion comprising:
   liposomes comprising 1,2-di-(9Z-octadecenoyl)-sn-glycero-3-phosphoethanolamine (DOPE) and at least one cationic lipid selected from the group consisting of 1,2-di-O-octadecenyl-3-trimethylammoniumpropane (DOTMA) and 1,2-dioleoyl-3-trimethylammoniumpropane (DOTAP), and
   at least one pH adjusting agent comprising an acid or an acidic buffer;
   wherein:
   a molar ratio of the at least one cationic lipid to DOPE is from about 1:4 to about 4:1; and
   the pH of the aqueous liposome dispersion is from about 2 to about 5.5.

2. The aqueous liposome dispersion of claim 1, wherein the liposomes have an average diameter from about 200 nm to about 600 nm.

3. The aqueous liposome dispersion of claim 1, wherein the at least one pH adjusting agent comprises an acid.

4. The aqueous liposome dispersion of claim 3, wherein the acid is acetic acid.

5. The aqueous liposome dispersion of claim 1, wherein the at least one pH adjusting agent comprises an acidic buffer.

6. The aqueous liposome dispersion of claim 5, wherein the acidic buffer is acetate buffer.

7. The aqueous liposome dispersion of claim 1, wherein the at least one pH adjusting agent is associated with the liposomes.

8. The aqueous liposome dispersion of claim 1, wherein the cationic lipid is DOTMA.

9. The aqueous liposome dispersion of claim 1, wherein the cationic lipid is DOTAP.

10. The aqueous liposome dispersion of claim 1, wherein the aqueous liposome dispersion has a pH that is about 3 to about 4.5.

11. The aqueous liposome dispersion of claim 1, wherein the aqueous liposome dispersion is characterized in that the hydrolysis rate of DOPE in the liposomes is reduced as compared to its hydrolysis rate at a pH between about 6 and 7.

12. The aqueous liposome dispersion of claim 1, wherein the aqueous liposome dispersion is characterized in that the hydrolysis rate of DOTAP in the liposomes is reduced as compared to its hydrolysis rate at a pH between about 6 and 7.

13. A kit comprising:
    (i) a first container comprising an aqueous liposome dispersion, wherein the aqueous liposome dispersion comprises:
        liposomes comprising 1,2-di-(9Z-octadecenoyl)-sn-glycero-3-phospho-ethanolamine (DOPE) and at least one cationic lipid selected from the group consisting of 1,2-di-Ooctadecenyl-3-trimethylammoniumpropane (DOTMA) and 1,2-dioleoyl-3-trimethylammoniumpropane (DOTAP), and
        at least one pH adjusting agent comprising an acid or an acidic buffer;
    wherein:
        a molar ratio of the at least one cationic lipid to DOPE is from about 1:4 to about 4:1; and
        the pH of the aqueous liposome dispersion is from about 2 to about 5.5; and
    (ii) a second container comprising a nucleic acid in a buffered solution having a pH from about 6 to about 8.

14. The kit of claim 13, wherein the at least one pH adjusting agent comprises an acidic buffer.

15. The kit of claim 14, wherein the acidic buffer is acetate buffer.

16. The kit of claim 13, wherein the cationic lipid is DOTMA.

17. The kit of claim 13, wherein the cationic lipid is DOTAP.

18. The kit of claim 13, wherein the nucleic acid is RNA.

19. The kit of claim 18, wherein the RNA is messenger RNA (mRNA), transfer RNA (tRNA), ribosomal RNA (rRNA), small nuclear RNA (snRNA), small inhibitory RNA (siRNA), small hairpin RNA (shRNA), microRNA (miRNA), antisense RNA, immunostimulating RNA (isRNA), or RNA aptamers.

20. The kit of claim 19, wherein the RNA is mRNA.

* * * * *